United States Patent
Taylor et al.

(10) Patent No.: US 11,116,656 B2
(45) Date of Patent: Sep. 14, 2021

(54) THERMAL CONTROL SYSTEM

(71) Applicant: Stryker Corporation, Kalamazoo, MI (US)

(72) Inventors: Gregory S. Taylor, Kalamazoo, MI (US); Christopher John Hopper, Kalamazoo, MI (US); Marco Constant, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 334 days.

(21) Appl. No.: 15/616,574

(22) Filed: Jun. 7, 2017

(65) Prior Publication Data

US 2017/0348144 A1    Dec. 7, 2017

Related U.S. Application Data

(60) Provisional application No. 62/346,583, filed on Jun. 7, 2016.

(51) Int. Cl.
| | |
|---|---|
| *A61F 7/00* | (2006.01) |
| *A61F 7/08* | (2006.01) |
| *A61F 7/02* | (2006.01) |

(52) U.S. Cl.
CPC .............. *A61F 7/0085* (2013.01); *A61F 7/02* (2013.01); *A61F 7/08* (2013.01); *A61F 7/0097* (2013.01);
(Continued)

(58) Field of Classification Search
CPC .. A61F 7/0085; A61F 7/08; A61F 7/02; A61F 7/0097; A61F 2007/0054;
(Continued)

(56) References Cited

U.S. PATENT DOCUMENTS

| | | |
|---|---|---|
| 5,227,988 A | 7/1993 | Sasaki et al. |
| 5,425,375 A | 6/1995 | Chin et al. |

(Continued)

FOREIGN PATENT DOCUMENTS

| | | |
|---|---|---|
| CA | 2393880 A1 | 1/2004 |
| CN | 202870824 U | 4/2013 |

(Continued)

OTHER PUBLICATIONS

Arctic Sun 2000, Medivance Arctic Sun Temperature Management System Operator's Manual, 2007.

(Continued)

*Primary Examiner* — Ronald Hupczey, Jr.
*Assistant Examiner* — Tigist S Demie
(74) *Attorney, Agent, or Firm* — Warner Norcross + Judd LLP

(57) ABSTRACT

A thermal control unit controls the temperature of a fluid delivered to one or more thermal transfer devices (e.g. thermal pads) in contact with a patient. The thermal control unit generates thermal data while being used to treat the patient and is adapted to receive thermal history data previously generated by a different thermal control unit in the treatment of that patient. Both the current and previous thermal data are displayable on the thermal control unit currently being used, thereby giving the caregiver a complete picture of the thermal history of the patient. The thermal control unit may also be adapted to transmit its thermal data, as well as the thermal history data previously received from the other thermal control unit, to still another thermal control unit. The thermal history data transfer may take place via a cable, wirelessly, by a portable flash drive, or by other means.

17 Claims, 9 Drawing Sheets

(52) U.S. Cl.
CPC ............... *A61F 2007/0054* (2013.01); *A61F 2007/0093* (2013.01); *A61F 2007/0095* (2013.01); *A61F 2007/0295* (2013.01)

(58) Field of Classification Search
CPC ...... A61F 2007/0093; A61F 2007/0095; A61F 2007/0295
See application file for complete search history.

(56) References Cited

U.S. PATENT DOCUMENTS

| | | | |
|---|---|---|---|
| 5,582,588 A | 12/1996 | Sakurai et al. | |
| 5,687,717 A | 11/1997 | Halpern et al. | |
| 5,720,293 A | 2/1998 | Quinn et al. | |
| 5,844,488 A | 12/1998 | Musick | |
| 5,877,675 A | 3/1999 | Rebstock et al. | |
| 6,149,674 A | 11/2000 | Borders | |
| 6,165,173 A | 12/2000 | Kamdar et al. | |
| 6,183,417 B1 | 2/2001 | Geheb et al. | |
| 6,261,261 B1 | 7/2001 | Gordon | |
| 6,542,767 B1 | 4/2003 | McNichols et al. | |
| 6,620,189 B1 | 9/2003 | Machold et al. | |
| 6,622,151 B1 | 9/2003 | Hamamoto et al. | |
| 6,671,535 B1 | 12/2003 | McNichols et al. | |
| 6,673,098 B1 | 1/2004 | Machold et al. | |
| 6,692,518 B2 | 2/2004 | Carson | |
| 6,878,156 B1 | 4/2005 | Noda | |
| 6,899,103 B1 | 5/2005 | Hood et al. | |
| 7,258,662 B2 | 8/2007 | Machold et al. | |
| 7,319,386 B2 | 1/2008 | Collins, Jr. et al. | |
| 7,594,925 B2 | 9/2009 | Danek et al. | |
| 7,598,853 B2 | 10/2009 | Becker et al. | |
| 7,666,215 B2 | 2/2010 | Callister et al. | |
| 7,708,768 B2 | 5/2010 | Danek et al. | |
| 7,714,728 B2 | 5/2010 | Koblasz | |
| 7,860,968 B2 | 12/2010 | Bornhoevd et al. | |
| 8,019,965 B2 | 9/2011 | Agombar et al. | |
| 8,082,160 B2 | 12/2011 | Collins, Jr. et al. | |
| 8,100,957 B2 | 1/2012 | Callister et al. | |
| 8,102,254 B2 | 1/2012 | Becker et al. | |
| 8,120,471 B2 | 2/2012 | Collins, Jr. et al. | |
| 8,121,856 B2 | 2/2012 | Huster et al. | |
| 8,128,595 B2 | 3/2012 | Walker et al. | |
| 8,249,547 B1 | 8/2012 | Fellner | |
| 8,249,894 B2 | 8/2012 | Brown | |
| 8,281,433 B2 | 10/2012 | Riley et al. | |
| 8,287,452 B2 | 10/2012 | Young et al. | |
| 8,312,877 B2 | 11/2012 | Elaz et al. | |
| 8,313,461 B2 | 11/2012 | Walker et al. | |
| 8,435,277 B2 | 5/2013 | Schock et al. | |
| 8,444,558 B2 | 5/2013 | Young et al. | |
| 8,451,101 B2 | 5/2013 | Somasundaram et al. | |
| 8,484,429 B2 | 7/2013 | Kassai | |
| 8,523,927 B2 | 9/2013 | Levinson et al. | |
| 8,639,307 B2 | 1/2014 | Fein et al. | |
| 8,672,853 B2 | 3/2014 | Young | |
| 8,756,078 B2 | 6/2014 | Collins, Jr. et al. | |
| 8,870,819 B2 | 10/2014 | Walker et al. | |
| 8,926,561 B2 | 1/2015 | Verhoef et al. | |
| 8,968,378 B2 | 3/2015 | Ginsburg et al. | |
| 9,135,208 B1 | 9/2015 | Huang et al. | |
| 9,147,334 B2 | 9/2015 | Long et al. | |
| 9,159,148 B2 | 10/2015 | Boyer et al. | |
| 9,179,863 B2 | 11/2015 | Brauers et al. | |
| 9,199,091 B2 | 12/2015 | Danek et al. | |
| 9,218,454 B2 | 12/2015 | Kiani et al. | |
| 9,230,421 B2 | 1/2016 | Reeder et al. | |
| 9,233,222 B2 | 1/2016 | Elaz et al. | |
| 9,259,349 B2 | 2/2016 | Walker et al. | |
| 9,278,024 B2 | 3/2016 | Scott et al. | |
| 9,278,183 B2 | 3/2016 | Pirzada | |
| 9,314,367 B2 | 4/2016 | Callister et al. | |
| 9,317,662 B2 | 4/2016 | Bangera et al. | |
| 9,320,444 B2 | 4/2016 | Hayes | |
| 2002/0014951 A1 | 2/2002 | Kramer et al. | |
| 2004/0064169 A1 | 4/2004 | Briscoe et al. | |
| 2005/0102167 A1 | 5/2005 | Kapoor | |
| 2006/0049936 A1 | 3/2006 | Collins, Jr. et al. | |
| 2006/0122673 A1 | 6/2006 | Callister et al. | |
| 2007/0130692 A1 | 6/2007 | Lemire et al. | |
| 2007/0268955 A1 | 11/2007 | Pohl et al. | |
| 2008/0255641 A1 | 10/2008 | Ellis | |
| 2009/0018626 A1 | 1/2009 | Levinson et al. | |
| 2009/0112630 A1 | 4/2009 | Collins, Jr. et al. | |
| 2009/0243833 A1 | 10/2009 | Huang et al. | |
| 2009/0322513 A1 | 12/2009 | Hwang et al. | |
| 2010/0052917 A1 | 3/2010 | Sullivan et al. | |
| 2010/0079276 A1 | 4/2010 | Collins, Jr. et al. | |
| 2010/0117823 A1 | 5/2010 | Wholtjen | |
| 2010/0170043 A1 | 7/2010 | Young et al. | |
| 2011/0060221 A1 | 3/2011 | Fan et al. | |
| 2011/0060328 A1 | 3/2011 | Skwarek et al. | |
| 2011/0144455 A1 | 6/2011 | Young et al. | |
| 2011/0210925 A1 | 9/2011 | Pittenger et al. | |
| 2012/0072238 A1 | 3/2012 | Collins, Jr. et al. | |
| 2012/0092135 A1 | 4/2012 | Collins, Jr. et al. | |
| 2012/0119890 A1 | 5/2012 | Collins, Jr. et al. | |
| 2012/0172956 A1* | 7/2012 | Dewaegenaere | A61B 18/00 607/104 |
| 2013/0102963 A1 | 4/2013 | Marsh et al. | |
| 2013/0283529 A1* | 10/2013 | Hayes | A61G 7/018 5/600 |
| 2013/0297217 A1 | 11/2013 | Bangera et al. | |
| 2013/0297219 A1 | 11/2013 | Bangera et al. | |
| 2014/0039351 A1 | 2/2014 | Mix et al. | |
| 2014/0046620 A1 | 2/2014 | Pompei et al. | |
| 2014/0052135 A1 | 2/2014 | Aman et al. | |
| 2014/0085082 A1 | 3/2014 | Lyon et al. | |
| 2014/0136755 A1 | 5/2014 | Hyde et al. | |
| 2014/0195057 A1 | 7/2014 | Zerhusen et al. | |
| 2014/0277308 A1 | 9/2014 | Cronise et al. | |
| 2014/0313030 A1 | 10/2014 | Ten Kate et al. | |
| 2014/0343639 A1* | 11/2014 | Hopper | A61F 7/0085 607/104 |
| 2014/0380012 A1 | 12/2014 | Sanford | |
| 2015/0008710 A1 | 1/2015 | Young et al. | |
| 2015/0105631 A1 | 4/2015 | Tran et al. | |
| 2015/0182114 A1 | 7/2015 | Wang et al. | |
| 2015/0186611 A1 | 7/2015 | George et al. | |
| 2015/0213324 A1 | 7/2015 | Amarasingham et al. | |
| 2015/0223705 A1 | 8/2015 | Sadhu | |
| 2015/0265366 A1 | 9/2015 | Andrews et al. | |
| 2015/0290060 A9 | 10/2015 | Hayes et al. | |
| 2016/0022218 A1 | 1/2016 | Hayes et al. | |
| 2016/0073889 A1 | 3/2016 | Belsinger, Jr. et al. | |
| 2016/0183794 A1* | 6/2016 | Gannon | A61B 5/0008 600/549 |
| 2016/0235367 A1 | 8/2016 | Kolar et al. | |

FOREIGN PATENT DOCUMENTS

| | | |
|---|---|---|
| CN | 204181603 U | 3/2015 |
| EP | 0553372 A1 | 1/1992 |
| EP | 1623666 B1 | 9/2009 |
| EP | 2660744 A1 | 11/2013 |
| EP | 3058869 A1 | 8/2016 |
| JP | 2004514464 A | 5/2004 |
| JP | 4072343 B2 | 4/2008 |
| WO | 9718639 | 5/1997 |
| WO | 9834577 | 8/1998 |
| WO | 2003105095 A2 | 12/2003 |
| WO | 2004093023 A2 | 10/2004 |
| WO | 2004104619 A1 | 12/2004 |
| WO | 2009029996 A1 | 3/2009 |
| WO | 2009055635 A1 | 4/2009 |
| WO | 2014081276 A1 | 5/2014 |
| WO | 2014189941 A1 | 11/2014 |

OTHER PUBLICATIONS

Gaymar Medi-Therm III, Hyper/Hypothermia Machine Ref MTA7912 Service Manual, Nov. 2009.
Arctic Sun 5000, Medivance Service Manual, 2010-2011.

(56) References Cited

OTHER PUBLICATIONS

Arctic Sun 5000 Temperature Management System, Medivance Service Manual, Jun. 2013.
Heater-Cooler System 3T, Sorin Group Operating Instructions, Feb. 2015.
Altrix Precision Temperature Management System, Stryker Operations Manual, Dec. 2016.
International Search Report for PCT/US2017/035948, the international counterpart to U.S. Appl. No. 15/616,574.
International Written Opinion for PCT/US2017/035948, the international counterpart to U.S. Appl. No. 15/616,574.
Spot Vital Signs Device, welchallyn.com, dated Jun. 6, 2017.
European Search Report, dated Dec. 3, 2019, for EP patent application EP17810784, a foreign counterpart.

* cited by examiner

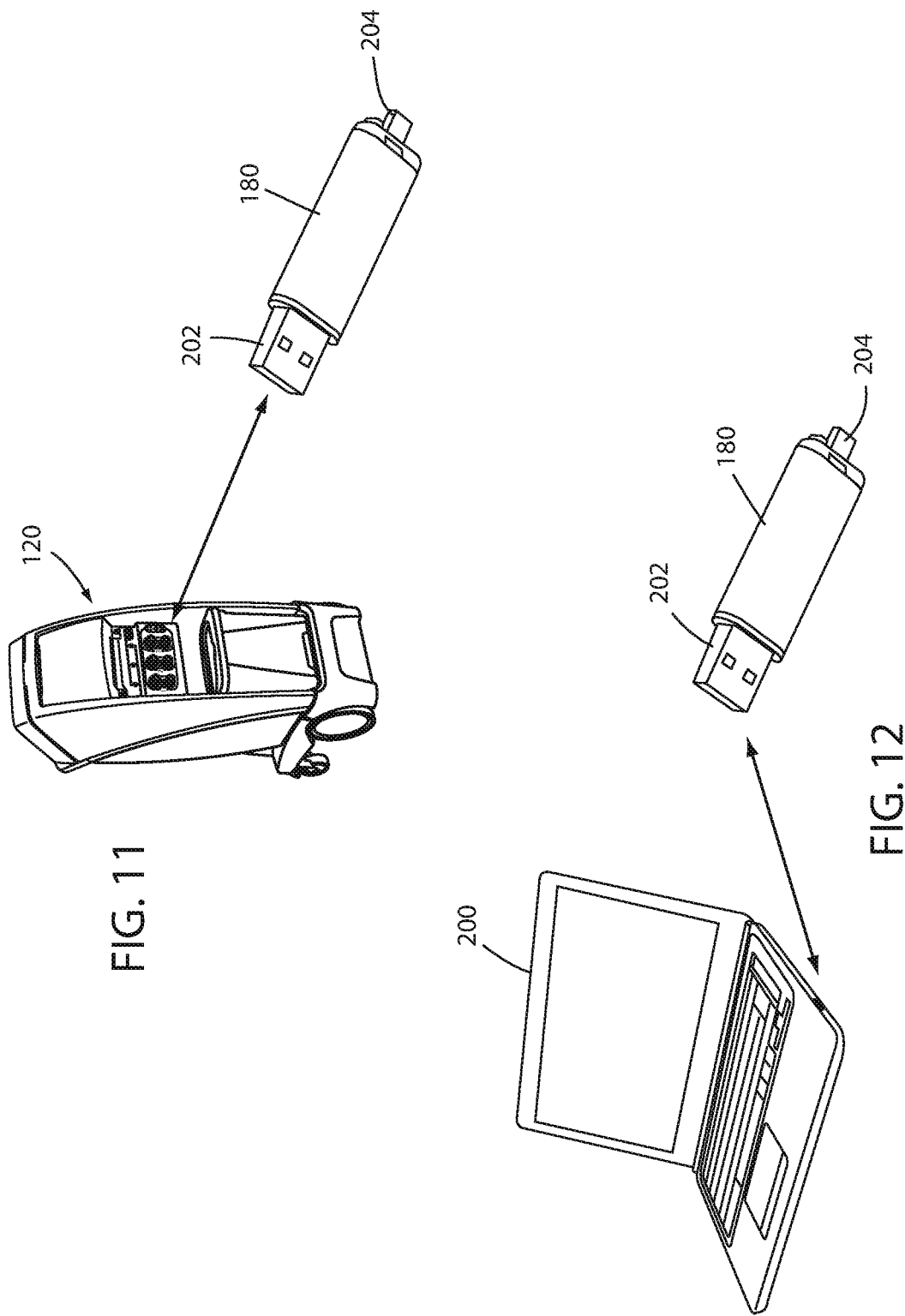

THERMAL CONTROL SYSTEM

CROSS-REFERENCE TO RELATED APPLICATIONS

This application claims priority to U.S. provisional patent application Ser. No. 62/346,583 filed Jun. 7, 2016, by inventors Gregory S. Taylor et al. and entitled THERMAL CONTROL SYSTEM, the complete disclosure of which is incorporated herein by reference.

BACKGROUND

The present disclosure relates to a thermal control system for controlling the temperature of circulating fluid which is delivered to one or more thermal pads positioned in contact with a patient.

Thermal control systems are known in the art for controlling the temperature of a patient by supplying temperature controlled fluid to one or more pads, blankets, or similar structures, that are positioned in contact with a patient. The temperature of the fluid is controlled by a thermal control unit that provides fluid to the pads or blankets. After passing through the pads or blankets, the fluid is returned to the thermal control unit where any necessary adjustments to the returning fluid temperature are made before being pumped back to the pad or blanket. In some instances, the temperature of the fluid is controlled to a target temperature, while in other instances the temperature of the fluid is controlled in order to effectuate a target patient temperature. When controlling a patient's temperature, a patient temperature probe may be attached to the control unit in order to provide patient temperature readings as feedback to the control unit so that it can make the necessary temperature adjustments to the fluid.

When patients undergoing thermal treatment move from an ambulance to a medical facility, or from one location within a medical facility to another, or from one medical facility to another medical facility, they often are disconnected from a first thermal control unit that was applied at the first location and connected to a second thermal control unit that is connected at the second location. For example, when a patient undergoing thermal treatment arrives at a medical facility via an ambulance (or helicopter, or other emergency transport), the patient is typically coupled to a smaller, less-featured thermal control unit. Upon arrival at the hospital, however, the patient may be coupled to a larger, more feature-rich, thermal control unit. Once at the hospital, additional transfers between thermal control units may occur during transport of the patient from one location to another within the hospital, or when transporting the patient to a different hospital or medical facility.

SUMMARY

The present disclosure provides various improved aspects for sharing data gathered from a first thermal control unit with a second thermal control unit. The first unit is adapted to generate thermal data while it is being used to control the temperature of a patient. When the patient is subsequently switched to having his or her temperature controlled by a second thermal control unit, the thermal data generated by the first thermal control unit is easily transferred to the second thermal control unit, thereby enabling the caregiver to view the thermal data generated from the first thermal control unit on one or more displays of the second thermal control unit. In this manner, the caregiver is able to see an entire thermal history of the patient on one device, thereby giving the caregiver a complete summary of thermal events and other important thermal data regarding the treatment of the patient.

According to one embodiment of the present disclosure, a thermal control unit for supplying temperature controlled fluid to a thermal pad is provided. The thermal control unit includes a fluid outlet adapted to fluidly couple to a fluid supply line, a fluid inlet adapted to fluidly couple to a fluid return line, a heat exchanger, a pump, a transceiver, a memory, a display, and a controller. The pump circulates the fluid from the fluid inlet through the heat exchanger and to the fluid outlet. The controller is adapted to receive previous thermal history data from a secondary thermal device via the transceiver and display the previous thermal history data on the display.

The thermal history data includes one or more of the following data items: a patient target temperature; a fluid target temperature; a plurality of previous patient temperature readings; a plurality of previous fluid temperature readings; a time at which previous thermal treatment started; a time at which previous thermal treatment ended; a flow rate of the fluid; a rate of change of a patient's temperature; a rate of change of the fluid's temperature; a time at which a plurality of temperature readings were taken; one or more alarms or errors; and an identification of the secondary thermal device.

Additional data may also be included with the thermal history data, or as a separate set of data that gets stored, transferred, and/or displayed along with thermal history data. The additional data may include any one or more of the following: the patient's heart rate, breathing rate, oxygenation levels, other vital signs of the patient, medications administered, time of Return Of Spontaneous Circulation (ROSC), and/or the history and times of any one or more of these items.

According to other aspects of the disclosure, the thermal control unit includes a port in communication with the transceiver. The port receives a physical communication medium that delivers the previous thermal history data to the transceiver. The physical communication medium may be a serial communication transceiver, such as, but not limited to, a flash memory device in which the previous thermal history data is stored, or a cable coupled to the second thermal device. When implemented as a flash memory device, the flash memory device is a portable device adapted to be able to plug into a secondary port on the secondary thermal device.

In other embodiments, the transceiver is a wireless transceiver.

The thermal control unit is, in some embodiments, further adapted to record primary thermal history data generated from using the thermal control unit and to display the primary thermal history data on the display. The controller is programmed to display the primary thermal history data and the previous thermal history data in different manners such that a viewer of the display is provided a visual indication of whether the displayed thermal history data corresponds to the primary thermal history data or the previous thermal history data.

The control unit is further adapted, in at least some embodiments, to be able to forward both the primary thermal history data and the previous thermal history data to another device. When forwarding the primary thermal history data, the controller forwards a primary device ID identifying the thermal control unit. When forwarding the previous thermal history data, the controller forwards a secondary device ID that identifies the secondary thermal device.

The secondary thermal device is adapted, in some embodiments, to control a temperature of a patient being treated by the secondary thermal device. When so adapted, the secondary thermal device includes a pump, a heat exchanger, and a fluid whose temperature is controlled by the heat exchanger of the secondary thermal device.

The thermal control unit also includes, in some embodiments, a user interface adapted to enable a user of the thermal control unit to allow or disallow receiving the previous thermal history data.

The secondary thermal device is a thermal pad, in some embodiments. The thermal pad includes an inlet port adapted to fluidly couple to the fluid outlet of the thermal control unit, an outlet port adapted to fluidly coupled to the fluid inlet of the thermal control unit, and an internal flow channel by which fluid received from the inlet port travels to the outlet port. The thermal pad further includes a memory for storing the previous thermal history data.

In some cases, the thermal pad receives the previous thermal history data from a tertiary thermal device that includes a pump, a heat exchanger, and a fluid whose temperature is controlled by the heat exchanger of the tertiary thermal device. The fluid of the tertiary thermal device is pumped by the tertiary thermal device to the inlet port of the thermal pad.

The thermal pad is adapted to wrap around a portion of a patient's body, in some embodiments, and to receive temperature controlled fluid from the thermal control unit.

The controller records a time at which previous thermal history data was received from the secondary thermal device and is adapted to display the time on the display.

The controller of the thermal control unit, in some embodiments, is adapted to send, in response to a user prompt, a request to the secondary thermal device for the previous thermal history data.

According to another embodiment, a thermal pad is provided that includes a flexible body, a fluid inlet, a fluid outlet, a transceiver, a memory, and a controller. The flexible body is adapted to be placed in contact with the patient and defines an interior in which fluid circulates. The fluid inlet is in fluid communication with the flexible body and is adapted to receive the fluid from a thermal control unit adapted to control a temperature of the fluid. The fluid outlet is in fluid communication with the flexible body and adapted to return the fluid to the thermal control unit. The controller receives and stores in the memory thermal data received from the thermal control unit. The thermal data relates to therapy applied to the patient using the thermal pad.

In other aspects, the thermal data is generated from a sensor on-board the thermal control unit.

The controller is adapted to transfer the thermal data to another device, in some embodiments. The another device may comprise a second thermal control unit adapted to control a temperature of a fluid delivered from the second thermal control unit to the thermal pad. In such embodiments, the controller is further adapted to receive and store in the memory additional thermal data received from the second thermal control unit. The additional thermal data relates to therapy applied to the patient using the thermal pad while the thermal pad is coupled to the second thermal control unit. The controller is further adapted to separately maintain in the memory the thermal data and the additional thermal data.

The transceiver may be either a transceiver for wired communication or for wireless communication, or for both.

The thermal pad may further include a clock in communication with the controller that is adapted to record times at which the thermal data is received from the thermal control unit.

According to another embodiment, a thermal control unit is provided for supplying temperature controlled fluid to a thermal pad. The thermal control unit includes a fluid outlet, a fluid inlet, a heat exchanger, a pump, a transceiver, a first memory, and a controller. The fluid outlet is adapted to fluidly couple to a fluid supply line for the thermal pad. The fluid inlet is adapted to fluidly couple to a fluid return line for the thermal pad. The pump circulates a fluid from the fluid inlet through the heat exchanger and to the fluid outlet. The controller records thermal data in the first memory relating to therapy applied to a patient using the thermal pad. The controller also is adapted to transfer the thermal data via the transceiver to a second memory stored on board the thermal pad.

According to other aspects, the controller periodically transfers the thermal data to the second memory while the fluid is being pumped from the thermal control unit to the thermal pad.

In some embodiments, the controller is further adapted to transfer an identifier identifying the thermal control unit to the second memory.

The controller may further be adapted to prevent the fluid from being pumped out of the fluid outlet until the controller detects that the transceiver is in communication with the thermal pad.

According to still another embodiment, a method of applying thermal therapy to a patient is provided. The method includes supplying temperature controlled fluid from a first thermal control unit to a thermal pad wrapped around a portion of the patient; recording thermal data in a first memory of the first thermal control unit wherein the thermal data relates to the supply of temperature controlled fluid from the first thermal control unit to the thermal pad; disconnecting the thermal pad from the first thermal control unit and connecting the thermal pad to a second thermal control unit; transferring the thermal data from the first memory to a second memory located off-board the first thermal control unit; and displaying the thermal data on a display coupled to a second thermal control unit.

According to other aspects, the second memory is located on the thermal pad and the thermal pad further transfers the thermal data to the second thermal control unit.

Alternatively, in other embodiments, the second memory is located on board the second thermal control unit.

In some embodiments, the method further includes supplying temperature controlled fluid from the second thermal control unit to the thermal pad. The method may also include recording second thermal data in the second memory wherein the second thermal data relates to the supply of temperature controlled fluid from the second thermal control unit to the thermal pad. Still further, in some embodiments, the method includes displaying the second thermal data on the display coupled to the second thermal control unit. When so displayed, the thermal data may be displayed with a first indicator and the second thermal data may be displayed with a second indicator. The first indicator indicates that the thermal data came from the first thermal control unit, and the second indicator indicates that the second thermal data came from the second thermal control unit.

The method may further include transferring the thermal data and the second thermal data to a third memory located on another thermal device.

Before the various embodiments disclosed herein are explained in detail, it is to be understood that the claims are not to be limited to the details of operation or to the details of construction, nor to the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 11 is a diagram of a thermal control unit communicating with a Universal Serial Bus (USB) device; and FIG. 12 is a diagram of the USB device of FIG. 11 communicating with a laptop computer.

DETAILED DESCRIPTION OF THE EMBODIMENTS

Figure 1:
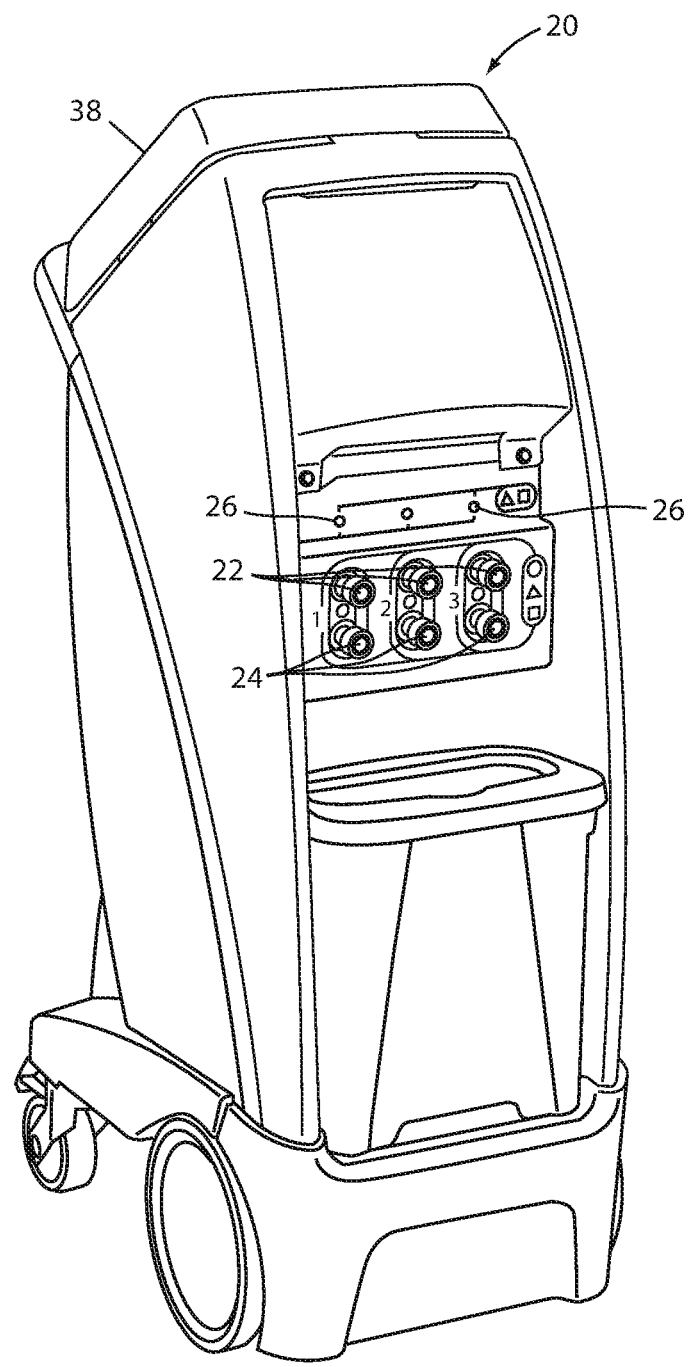
FIG. 1 is a perspective view of a first thermal control unit according to one aspect of the present disclosure.

A thermal control unit 20 according to one embodiment of the present disclosure is shown in FIG. 1. Thermal control unit 20 is adapted to provide temperature controlled fluid to one or more thermal pads that are positioned in contact with a patient to thereby control the temperature of the patient. Thermal control unit 20 includes a plurality of fluid outlet ports 22, a plurality of fluid inlet ports 24, a plurality of patient temperature probe ports 26, and a user interface 38. The outlet ports 22 are adapted to be fluidly coupled to a corresponding fluid supply line 28a (FIG. 2) that transports the temperature controlled fluid from the thermal control unit 20 to a connected patient thermal therapy device 30, which may be a pad, a blanket, a vest, or other structure. For purposes of the following written description, the term "thermal pad" will be used to generically refer to any of these types of thermal therapy devices 30.

The inlet ports 24 are each adapted to be fluidly coupled to a corresponding fluid return line 28b that returns the temperature controlled fluid from the thermal pad 30 back to the control unit 20. Control unit 20 senses the temperature of the fluid returning via inlet ports 24 and either heats or cools the fluid, as necessary, in order to change the temperature of the fluid to a desired temperature. After any necessary changes are made to the fluid's temperature, control unit 20 pumps the fluid back to the thermal pad(s) 30. Control unit 20 therefore pumps temperature controlled fluid in one or more fluid circuits that are in thermal communication with the patient via one or more thermal pads 30.

Figure 2:
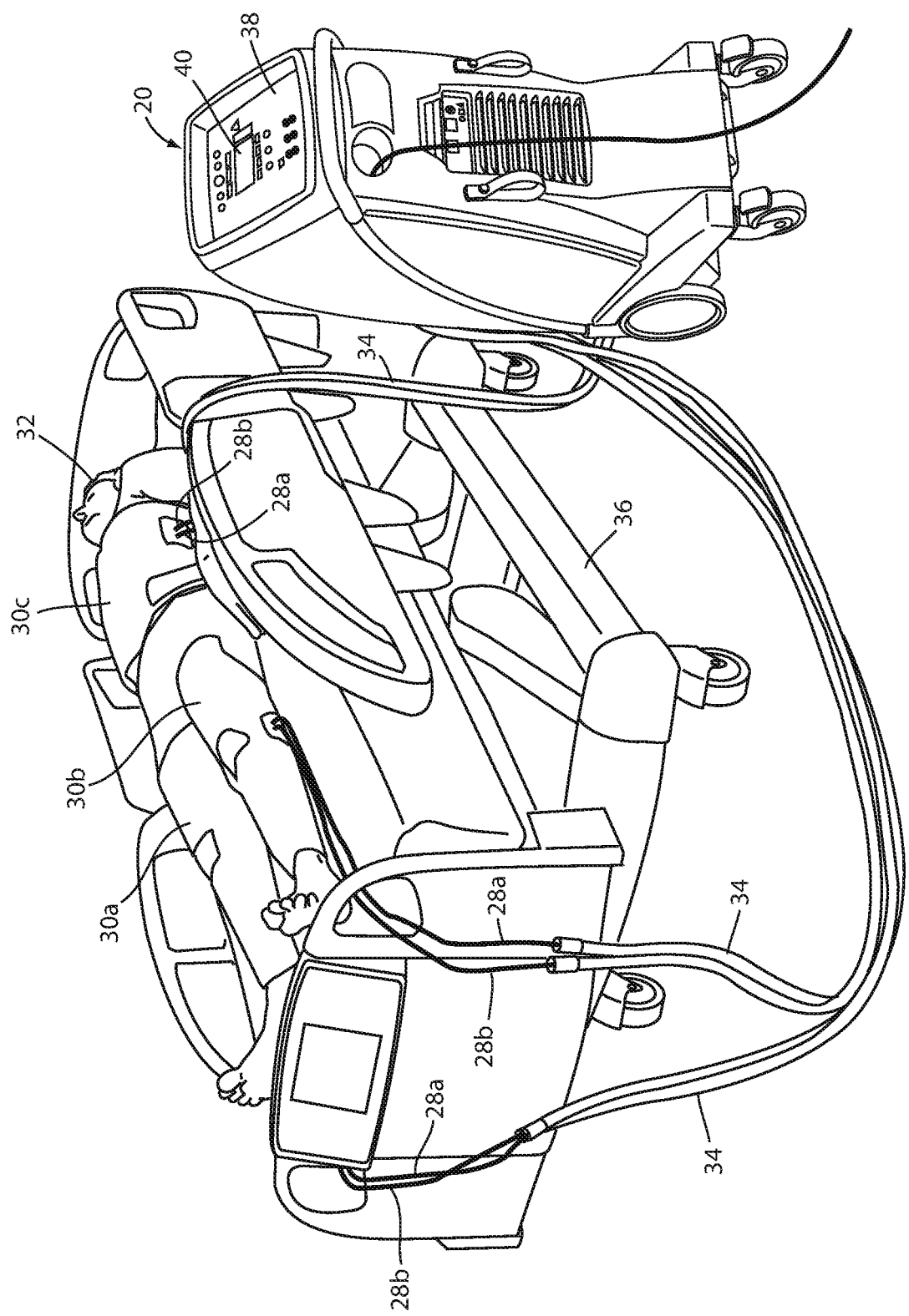
FIG. 2 is a perspective view of the thermal control unit of FIG. 1 shown fluidly connected to several thermal pads wrapped around a patient undergoing thermal treatment.

In the example illustrated in FIG. 2, thermal control unit 20 circulates temperature controlled fluid to three separate thermal pads 30a, b, and c. A first one of the thermal pads 30a is wrapped around the patient's right leg. A second one of the thermal pads 30b is wrapped around the patient's left leg. And a third one of the thermal pads 30c is wrapped around the patient's torso. Other configurations can be used and different numbers of thermal pads 30 may be used with thermal control unit 20, depending upon the number of inlet and outlet ports 24 and 22 that are included with thermal control unit 20. Still further, in some embodiments of thermal control unit 20, one or more branching connectors (not shown) may be coupled to a single pair of inlet and outlet ports 24 and 22, if desired, so that multiple lines 28 and multiple thermal pads 30 may be supplied via a single inlet/outlet pair.

In the embodiment shown in FIG. 1, the fluid that returns to control unit 20 from each return line 28b is mixed in a common manifold, and the temperature of that mixed fluid is controlled to a single desired temperature (which may vary, as will be described more below) by passing it through a heat exchanger inside of control unit 20. The temperature controlled fluid is then pumped to each of outlet ports 22 for delivery to each supply line 28a, so that the temperature of the fluid delivered to each outlet port 22 is the same. In this embodiment, each thermal pad 30 is supplied with fluid that is at the same temperature. In an alternative embodiment, control unit 20 is configured to be able to maintain temperature isolation between one or more of the fluid outlets 22 so that fluid of differing temperatures may be delivered from control unit 20 to the thermal pads 30.

It will also be understood by those skilled in the art that the number of ports 22 and 24 can be varied to include either a smaller or a greater number than the three illustrated in FIGS. 1 & 2. Still further, it will understood by those skilled in the art that the ports 22, 24 may be provided in various physical configurations and combinations to facilitate the connection and disconnection of the lines 28a, 28b and/or thermal pads 30. As but one example, instead of using a separate pair of ports 22 and 24 for each individual thermal pad 30a, 30b, and 30c, as shown in FIG. 2, it is possible to modify control unit 20 to include a single multi-tube outlet port 22 and a single multi-tube inlet port 24 that simultaneously couples and de-couples multiple sets of supply lines 28a and return lines 28b to and from control unit 20. Still other variations are possible.

The patient temperature probe ports 26 of thermal control unit 20 (FIG. 1) are adapted to couple to patient temperature probes that are used to sense the temperature of the patient at one or more locations of the patient's body. The patient temperature probes that couple to ports 26 may be any suitable patient temperature probe that is able to sense the temperature of the patient at the location of the probe. In one embodiment, the patient temperature probes may be conventional YSI 400 probes marketed by YSI Incorporated of Yellow Springs, Ohio, or probes that are YSI 400 compliant. In other embodiments, other conventional 400 series thermistors may be used, or still other types of probes. Regardless of the specific type of patient temperature probe used, each temperature probe is connected to a patient temperature probe port 26 positioned on control unit 20. Patient temperature probe ports 26 are in electrical communication with a controller 66 inside of control unit 20 that is adapted, in at least some situations, to use the temperature sensed by at least one of the probes to control the temperature of the fluid circulated through control unit 20 and pads 30.

User interface 38 of thermal control unit 20 includes, in the illustrated embodiment, a display 40 on which data, controls, and/or functions of the thermal control unit may be accessed (FIG. 2). Such controls include one or more controls enabling a user to turn control unit 20 on and off, as well as one or more controls enabling the user to select a target temperature for the fluid delivered to thermal pads 30. In some embodiments, user interface 38 also allows a user to select a target temperature for the patient being treated, rather than a specific target temperature for the fluid. When this feature is present, thermal control unit 20 makes automatic adjustments to the temperature of the fluid in order to bring the patient's temperature to the desired patient target temperature.

When the user has selected a target temperature for the fluid, thermal control unit 20 utilizes the selected target temperature, as well as the temperature readings from a water temperature sensor 44 or a patient temperature sensor 46, to generate and send commands to an internal heat exchanger 42 (FIGS. 7-10), as necessary, in order to cool and/or warm the fluid circulating through thermal control unit 20 and thermal pads 30 so that it meets the selected target temperature. In at least one embodiment, thermal control unit 20 implements closed-loop feedback control of heat exchanger 42 using the output from the temperature sensor(s) 44 and/or 46 such that the temperature of the circulating fluid is adjusted toward the target temperature. The closed loop feedback may take on multiple different forms, such as proportional-integral-derivative (PID) control, any variant thereof (e.g. proportional-integral (PI) control), or still other types of closed loop controls.

Thermal control unit 20 is adapted, in the illustrated embodiment, to operate in a plurality of different modes that are selectable by a user. In a first mode, known as a manual mode, the thermal control unit 20 controls the temperature of the liquid circulating through control unit 20—and thereby the temperature of the fluid delivered to thermal pads 30—so that it matches a target temperature chosen by the user. In this mode, control unit 20 maintains the liquid at the chosen target temperature regardless of the patient's temperature, and control unit 20 may be used without any patient temperature probes, if desired. In a second mode, known as an automatic mode, the thermal control unit 20 controls the temperature of the liquid circulating through control unit 20 in such a manner that a target patient temperature is achieved and/or maintained. In this automatic mode, at least one patient temperature probe or sensor 46 (FIGS. 7-10) is coupled to control unit 20 so that control unit 20 knows the patient's current temperature. In the automatic mode, control unit 20 does not necessarily adjust the temperature of the circulating fluid to maintain a constant temperature, but instead makes the necessary temperature adjustments to the fluid in order to reach, or maintain, the desired patient target temperature.

Further details about the construction and operation of one embodiment of thermal control unit 20 may be found in commonly assigned U.S. patent application Ser. No. 14/282,383 filed May 20, 2014, by inventors Christopher Hopper et al. and entitled THERMAL CONTROL SYSTEM, the complete disclosure of which is hereby incorporated herein by reference. Control unit 20 may alternatively be constructed and/or operate in other manners, including, but not limited to, any of the manners disclosed in commonly assigned U.S. Pat. No. 6,517,510 issued to Stewart and entitled AUTOMATIC PATIENT CONTROL DEVICE, or in commonly assigned U.S. Pat. No. 8,257,414 issued to Kelner et al. and entitled THERMAL PUMP WITH FEATURES, the disclosures of both of which are incorporated herein by reference. In still other embodiments, control unit 20 may be a control unit from any of the MEDI-THERM® hyper/hypothermia systems marketed Stryker Corporation of Kalamazoo, Mich. As another alternative, thermal control unit 20 may be a mobile thermal control unit that is constructed and/or operates in any of the manners disclosed in commonly assigned U.S. patent application Ser. No. 62/311,054 filed Mar. 21, 2016, by inventor Gregory Taylor and entitled MOBILE THERMAL SYSTEM, the complete disclosure of which is also incorporated herein by reference. Still other types of thermal control units may be used.

When thermal control unit 20 is being used to control a patient's temperature, it generates and records thermal data about the thermal treatment being applied to the patient. This thermal data includes any one or more of the following items: current and past patient target temperatures; current and past fluid target temperatures; current and past patient temperature readings; current and past fluid temperature readings; a time at which thermal treatment started; times at which the thermal treatment ended or changed; current and past flow rates of the fluid; current and past rates of change of the patient's temperature; current and past rates of change of the fluid's temperature; current and past modes (e.g. automatic or manual) in which the thermal control unit 20 has operated, or is operating; and any alarms or thermal events. Thermal control unit 20 also time and date stamps all of these readings and/or events that are part of this thermal data. Thermal control unit 20 also stores a unique identifier that uniquely distinguishes thermal control unit 20 from other thermal control units and associates this unique identifier with the aforementioned stored thermal data. Still other thermal data may be generated and stored by control unit 20.

Additional data may also be included with the thermal history data, or as a separate set of data that gets stored, transferred, and/or displayed along with the thermal history data. The additional data may include any one or more of the following: the patient's heart rate, breathing rate, blood pressure, metabolic rate, radiation history, caloric consumption, oxygenation levels, other vital signs, administered medications, applied therapy, Return Of Spontaneous Circulation (ROSC), and/or the history and times of any one or more of these items. Still other data may be included, such as an identification of the caregiver and/or other personnel who are, or have been, associated with the patient.

In addition to storing the thermal data, thermal control unit 20 is adapted to transfer this thermal data to another control unit that is subsequently used for treating the same patient. In this manner, the thermal data generated by a first thermal control unit 20 during the treatment of a patient can be transferred to a second thermal control unit 20 that is used to provide thermal treatment to the same patient. The second thermal control unit may also be adapted to store and record the thermal data it generates and make that thermal data available for a third thermal control unit 20 that is subsequently used to treat that same patient. When the second thermal control unit transfers its thermal data to the third thermal control unit 20, not only does it transfer the thermal data it generated during its treatment of the patient, but also the thermal data it received from the first thermal control data. The third thermal control unit, just like the first and second thermal control units, may also be adapted to transfer its thermal data, as well as the thermal data it received from the previous thermal control units 20 onto yet a fourth, fifth, or other thermal control unit. By including the ability to transfer thermal data to another thermal control unit and display the received thermal data, the caregiver(s) assigned to the patient are able to see the full thermal history of the patient on whichever thermal control unit 20 is currently being used to treat the patient.

In some embodiments, the thermal data that is transferred does not include any patient-identification information or any other Protected Health Information (PHI) that is subject to the privacy provisions of the United States' Health Insurance Portability and Accountability Act of 1996 (a.k.a. HIPAA). In an alternative embodiment, some of the thermal history data may include data that is considered Protected Health Information, and control units 20 and 20' and the communication links used to transfer data from one to the other are configured to ensure that appropriate safeguards are built into the data transfer subsystem to ensure compliance with HIPAA.

The transferred thermal history data enables a caregiver to see the full thermal history of a patient, which can be useful for determining whether to continue with a currently planned course of treatment, modify the treatment, and/or start a different treatment. In some embodiments, the thermal control unit is adapted to provide one or more suggestions for treating the patient based upon data contained within the thermal history data. The transfer of the thermal history from one or more previous devices also enables the caregiver to determine if there were any lapses in the patient's previous thermal treatment and, if so, to see when those lapses occurred and how long they lasted. Still further, in some embodiments, any of the thermal control units may be configured to automatically limit their functionality based upon one or more items of information contained within the patient's thermal history data.

Figure 3:
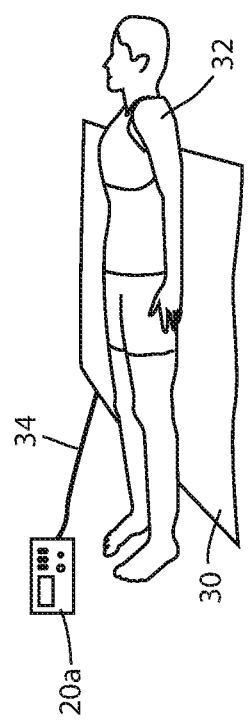
FIG. 3 is a diagram of a first thermal control unit, a thermal pad, and a patient shown at a first location, such as a location outside of a medical facility.
Figure 4:
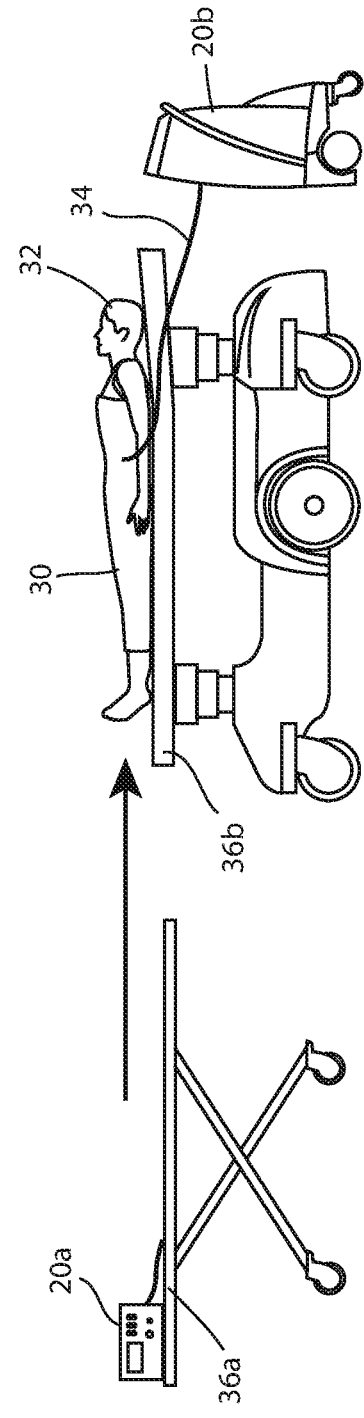
FIG. 4 is a diagram of the first thermal control unit, thermal pad, and patient of FIG. 3, as well as a second thermal control unit adapted to receive thermal data from the first thermal control unit, all of which are shown at a second location, such as a location inside of a medical facility.
Figure 5:
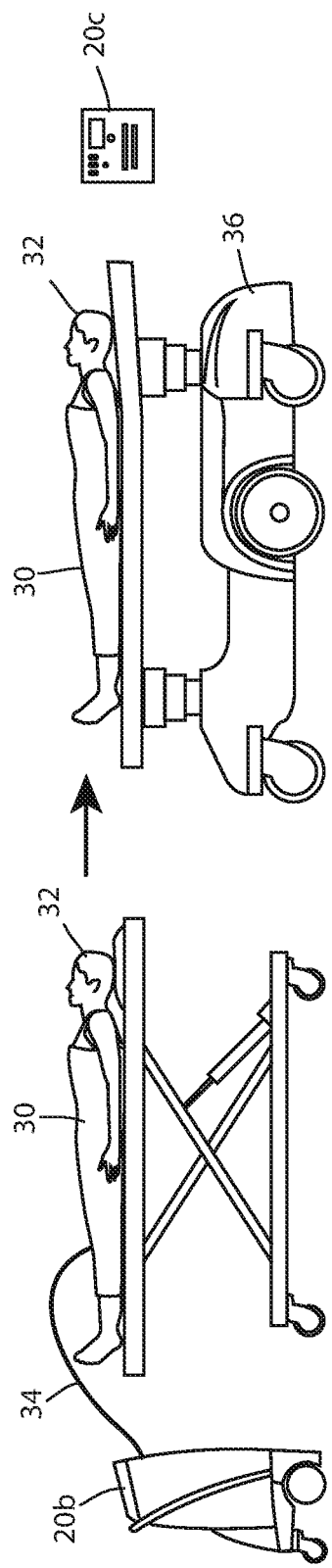
FIG. 5 is a diagram of the second thermal control unit and thermal pad of FIG. 4, as well as a third thermal control unit adapted to receive thermal data from the second thermal control unit.

FIGS. 3-5 illustrate one manner in which the thermal data from multiple thermal control units 20 may be passed onto each other. FIG. 3 illustrates a first thermal control unit 20a that is used with a thermal pad 30 on a patient 32. One or more hoses 34 housing one or more fluid supply and return lines 28a and 28b are coupled between first thermal control unit 20a and thermal pad 30. First thermal control unit 20a may be a portable thermal control unit of the type that can be easily transported and used in the field by emergency responders, or it may be another type of thermal control unit. When first thermal control unit 20a is fluidly coupled to a thermal pad 30 wrapped around a portion of patient 32, it pumps temperature controlled fluid to thermal pad 30 in order to control the temperature of patient 32. While supplying temperature controlled fluid to patient 32, first thermal control unit 20a generates thermal data, such as any one or more of the types of thermal data discussed above. First thermal control unit 20a saves this thermal data so that it can be transferred to a second thermal control unit, if desired.

FIG. 4 illustrates a second thermal control unit 20b that is used to treat the same patient 32 as the one shown in FIG. 3. Second thermal control unit 20b may a thermal control unit of the type more commonly found in a medical facility, such as a hospital, rather than a more mobile thermal control unit such as the type of thermal control unit that may be used by emergency responders. However, second thermal control unit 20b may also be a mobile thermal control unit and, in some embodiments, could even be the same type of thermal control unit as first thermal control unit 20a.

Regardless of its specific construction and type, second thermal control unit 20b is adapted to receive the thermal data generated by first thermal control unit 20a and to display some or all of this data on a display (not shown) coupled to second thermal control unit 20b. In the illustrated embodiment, second thermal control unit 20b is shown coupled to thermal pad 30, which is the same thermal pad 30 that first thermal control unit 20a was previously connected to when first thermal control unit 20a was treating patient 32. The use of the same thermal pad(s) 30 on the patient with different thermal control units 20 is common because removing the thermal pad(s) 30 and replacing them with different ones is labor and capital intensive, and often serves no purpose. It will, however, be understood that the principles discussed herein could be applied to situations where second thermal control unit 20b treats patient 32 with a different set of thermal pads 30. For purposes of the following discussion, however, it will be assumed that the same set of thermal pads 30 is used with the patient.

At some point shortly before or after the transfer of patient 32 from a first patient support apparatus 36a to a second patient support apparatus 36b (FIG. 4), the thermal data that was generated and stored in first thermal control unit 20a is transferred to second thermal control unit 20b. After it is transferred, second thermal control unit 20b stores it and makes some or all of it available for display on second thermal control unit 20b. In addition to displaying the received thermal data (hereinafter referred to as "thermal history data"), second control unit 20b also generates and records its own thermal data. That is, second control unit 20b records any of the aforementioned types of thermal data that are generated during its supplying of temperature controlled fluid to thermal pad 30. Some or all of this thermal data is also made available for display on second control unit 20b.

In some cases, patient 32 may need to be transferred to another location and treated with yet a third thermal control unit 20c (FIG. 5). Third thermal control unit 20c is, in the example shown in FIG. 5, constructed to receive and selectively display all or some of the thermal history data from second thermal control unit 20b and first thermal control unit 20a. The thermal history data that third thermal control unit 20c receives from second thermal control unit 20b not only includes the thermal data that was generated and recorded by second thermal control unit 20b during the treatment of patient 32 using second thermal control unit 20b, but also the thermal history data that was generated and recorded by first thermal control unit 20a during the treatment of patient 32 using first thermal control unit 20a. Accordingly, third thermal control unit 20c receives the entire thermal history data of the patient and makes some or all of this data available for display on a display incorporated into third thermal control unit 20c.

When a thermal control unit 20 receives thermal history data from another thermal control unit 20, it tags that data as having been received from the other thermal control unit and maintains that data separately from the thermal data that it itself generates. For example, in the examples of FIGS. 3-5, when second thermal control unit 20b receives thermal data from first thermal control unit 20a, second thermal control unit 20b segregates the thermal data received from first thermal control unit 20a from the thermal data it generates during its treatment of the patient. Such segregation may be accomplished in any known manner, including, but not limited to, an identifier being added to the thermal data in a particular field that indicates the source of the thermal data. In this manner, each thermal control unit 20 is able to determine and display to the caregiver the source of the thermal data.

Figure 6:
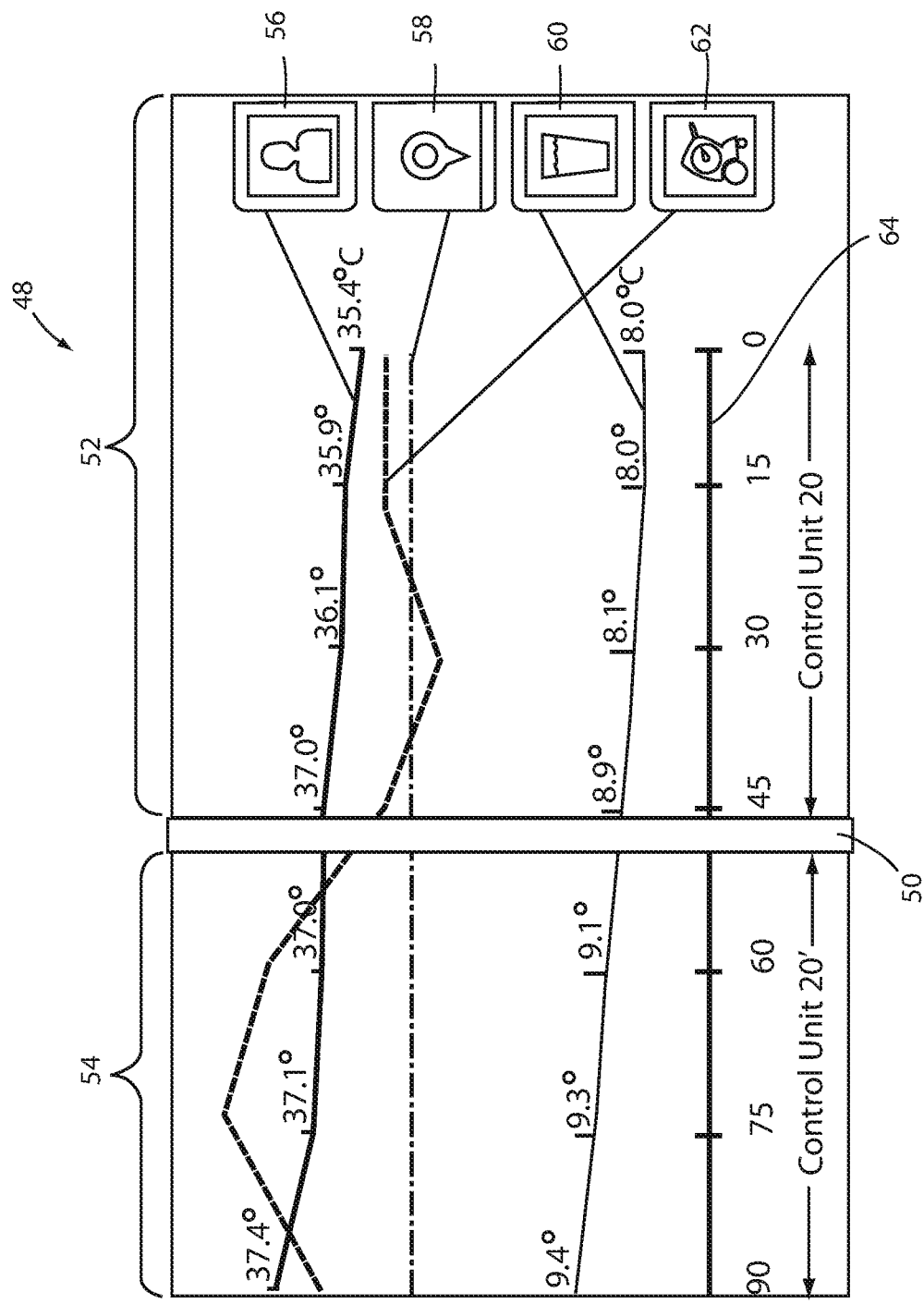
FIG. 6 is an illustrative screen shot of one manner in which first thermal data generated from a first thermal control unit may be displayed simultaneously with second thermal data generated from a second thermal control unit on a display of the second thermal control unit.

FIG. 6 illustrates one example of the type of thermal data that may be displayed on display 40 of any of the thermal control units 20, as well as one illustrative format for displaying that data. As shown therein, the format includes a side-by-side display of the thermal data generated from thermal control unit 20 the thermal data previously generated from a previously used thermal control unit 20'. More specifically, FIG. 6 illustrates an illustrative screen shot 48 that is displayable on display 40 of a control unit 20. Screen shot 48 includes a vertical divider 50 that separates screen shot 48 into a right portion 52 and a left portion 54. Right portion 52 displays data that is, and was, generated by the thermal control unit 20 on which screen shot 48 is being displayed. Left portion 54 displays thermal history data that was generated by a secondary thermal control unit 20' that was previously used to treat the same patient. Thus, the thermal data in right portion 52 was generated by thermal control unit 20 while the thermal data in left portion 54 was generated by thermal control unit 20'.

FIG. 6 further illustrates four graphs: a patient temperature graph 56, a patient target temperature graph 58, a water temperature graph 60, and a power level graph 62. All four of these graphs are plotted with respect to a horizontal time axis 64. A right end of time axis 64 corresponds to time zero (the current time) while a left end of time axis 64 corresponds, in this example, to a time ninety minutes previous to the current time. The scale of time axis 64 may, of course, vary.

The position of vertical divider 50 along time axis 64 varies in accordance with how long ago the transition between thermal control unit 20' and thermal control unit 20 occurred. In the illustrated embodiment, the transition of the patient from control unit 20' to control unit 20 occurred approximately 45 minutes ago. The width of vertical divider also varies in accordance with how much time the transition between control units 20' and 20 took. During this transition period, neither control unit 20 nor 20' was used to actively control the patient's temperature and there is, therefore, no temperature data to display on any of the four graphs 56-62 of FIG. 6. In the example shown in FIG. 6, the transition of the patient from thermal control unit 20' to thermal control unit 20 took less than five minutes.

Patient temperature graph 56 displays the temperature of the patient as sensed by one or more patient temperature sensors (e.g. probes) 46 that are coupled to temperature probe ports 26. Patient target temperature graph 58 displays the temperature that the caregiver has selected as the target for the patient. The selection of this target temperature is accomplished using user interface 38. Water temperature graph 60 displays the temperature of the water that is being delivered to thermal pads 30 from thermal control unit 20. Water temperature graph 60 is generated from one or more water temperature sensors 44 that are internal to thermal control units 20 and 20'. Power level graph 62 corresponds to how much electrical power thermal control units 20' and 20 is, or were, drawing and may be derived from any suitable source, such as, but not limited to, the amount of electrical current being drawn by heat exchanger 42. Power level graph 62 therefore provides an indication of how hard thermal control unit 20 (or 20') has had to work, or is working, to achieve the target temperature (either patient target temperature or water target temperature).

Screen shot 48 only displays a sampling of the types of thermal data generated from thermal control units 20 and 20' that may be displayed on display 40 of thermal control unit 20, as well as only one sample of the format in which such data may be displayed. Further, screen shot 48 display thermal data that is generated when thermal control units 20 and 20' are being used in the automatic mode. When these units are used in the manual mode, screen shot 48 will look different. Specifically, in the manual mode, there will be no patient target temperature graph 58. Instead, in one embodiment, patient target temperature graph 58 will be replaced by a water target temperature graph. Other changes may also take place.

The additional thermal data that may be displayed on display 40 includes any of the thermal data items discussed above. Still further, either or both of thermal control units 20 and 20' are adapted, in at least some embodiments, to flag any data or events that are of potential significance and store that data with the flags associated therewith. At least one of the user interfaces 38 of control units 20 or 20' includes a control that enables the caregiver to search through and selectively display the flagged data so that the caregiver doesn't have to review the entire thermal history data for events of potential significance. The control enables the caregiver to search through not only the thermal data that was generated by the thermal control unit 20 that is currently in use, but any and all previous thermal control units 20 that were used with the patient.

The events or data that are flagged by one or both of thermal control units 20 and 20' include a wide variety of different occurrences and data conditions. For example, one type of event that is flagged is any movement of the patient's temperature in a direction opposite to the temperature direction desired for the patient (e.g. if the patient's temperature increases while water colder than the patient's temperature is being applied to the patient's thermal pads 30, or vice versa). Another type of event is a power level that exceeds a predetermined threshold. Still other events of interest that are flagged include any errors (within control units 20 or 20' themselves, from patient temperature sensor 46, or from other sources), any patient temperature variations that exceeds one or more predetermined speeds, any drops or jumps in the fluid pressure of the temperature controlled fluid being supplied to thermal pads 30 that exceed one or more thresholds, any flow rates that change by more than a threshold, etc.

As noted, the format of the data shown in screen shot 48 may also be changed. In one variation, the data in right and left portions 52 and 54 may be displayed in different colors. In another variation, the thermal data from thermal control unit 20' may be displayed above or below the thermal data generated from thermal control unit 20, rather than side-by-side. Still other format variations are possible.

FIGS. 7-10 illustrate four different manners by which thermal data from a first thermal control unit 20' may be transferred to a second thermal control unit 20. FIGS. 7-10 also illustrate in greater detail the electrical components inside of each thermal control unit 20 and 20'. Although FIGS. 7-10 illustrate each thermal control unit 20 as having identical internal electrical components as thermal control unit 20', this is not necessarily the case. That is, thermal control units 20 and 20' may include different electrical components as long a first one of the thermal control units 20' is able to generate at least some thermal data for transferring to a second one of the thermal control units 20, and so long as thermal control unit 20 is able to receive such thermal history data. For purposes of the following description, however, each control unit 20 and 20' will be described as having the same components, and the same reference numbers for these components will be used for both control units 20 and 20'. A prime symbol (') will be placed after the components of thermal control unit 20' to distinguish them from the components of thermal control unit 20. Unless otherwise stated, each of the components from thermal control units 20 and 20' that bear the same reference number operate in the same manner and carry out the same functions.

Figure 7:
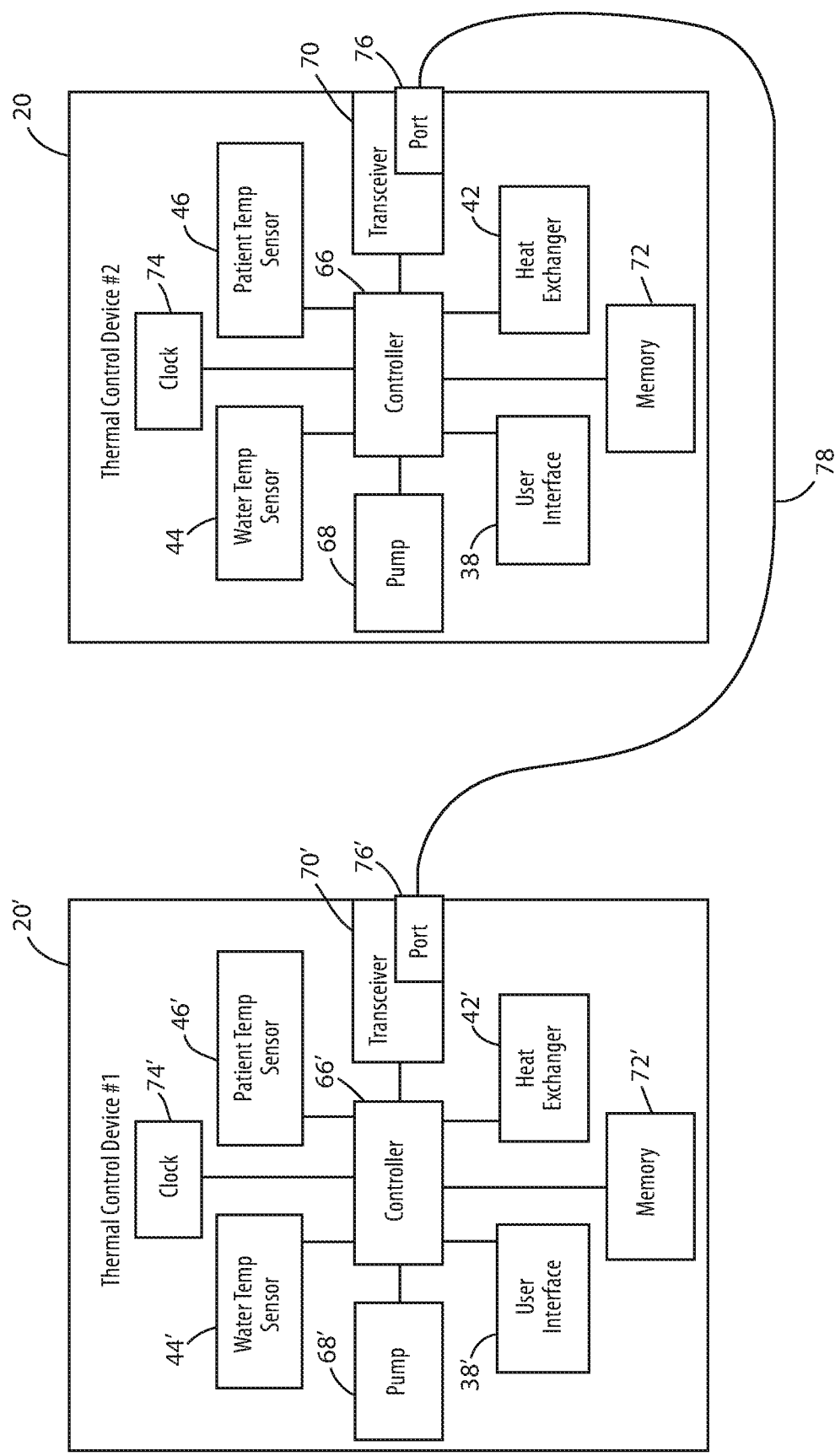
FIG. 7 is a block diagram of the electrical components of a pair of thermal control units illustrating a first manner for transferring thermal data between the two.

As shown in FIG. 7, each thermal control unit 20 includes a controller 66, a pump 68, a transceiver 70, a memory 72, and a clock 74, as well as user interface 38, one or more heat exchangers 42, water temperature sensor 44 and, in at least some embodiments, one or more patient temperature sensors 46. Controller 66 includes, in at least one embodiment, a microcontroller and accompanying circuitry for carrying out the functions and algorithms described herein, as would be known to one of ordinary skill in the art. In other embodiments, controller 66 may include one or more microprocessors and/or other programmable electronics that are programmed to carry out the functions described herein. It will be understood that controller 66 may also include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions in thermal control unit 20, or they may reside in a common location within thermal control unit 20. When physically distributed, the components may communicate using any suitable serial or parallel communication protocol, such as, but not limited to, CAN, LIN, Firewire, I-squared-C, RS-232, RS-485, universal serial bus (USB), etc.

Controller 66 uses the outputs from water temperature sensor 44 and patient temperature sensor 46 to control heat exchanger 42 so that the fluid flowing to thermal pads 30 has its temperature adjusted in the desired manner. Controller 66 also controls pump 68 which circulates the temperature controlled fluid through heat exchanger 42 and pumps it to thermal pads 30. Controller 66 is further programmed to record in memory 72 any one or more of the thermal data items discussed above. When recording such thermal data, controller 66 time and date stamps the recorded data using the time information supplied by clock 74.

Transceiver 70 provides the structure by which the thermal data generated by thermal control unit 20 during its treatment of a patient is transferred to another thermal control unit, as well as the structure by which thermal history data generated from a previous thermal control unit (e.g. thermal control unit 20') is received and stored in memory 72. As will be discussed in greater detail below, transceiver 70 may take on a wide variety of different forms. In the embodiment illustrated in FIG. 7, transceiver 70 includes a port 76 that is adapted to receive a data cable 78. Data cable 78 provides the communication medium by which the thermal history data from thermal control unit 20' is transferred to thermal control unit 20. Data cable 78 may be a conventional Ethernet cable, a USB cable, or any other cable suitable for transferring data.

In the example shown in FIG. 7, each of the thermal control units 20 and 20' includes one or more controls on their respective user interfaces 38 and 38' that allow the caregiver to control the transfer of thermal history data from thermal control unit 20' to thermal control unit 20. These controls include, in one embodiment, a "send" control on thermal control unit 20' that is activated by the caregiver in order to transfer the thermal history data, as well as a "receive" control on thermal control unit 20 that is also activated in order for thermal control unit 20 to receive this thermal history data. In order for the caregiver to transfer the thermal history data, the caregiver therefore first connects data cable 78 between the two thermal control units 20' and 20 and then activates the "send" and "receive" controls on the respective thermal control units 20' and 20. In some alternative embodiments, one or both of the "send" and "receive" commands need not be activated by the caregiver. Instead, control unit 20' automatically transfers its thermal history data to thermal control unit 20 whenever a cable, or other communication link (discussed more below) is established between the two control units 20 and 20'.

When sending its thermal history data to control unit 20, thermal control unit 20' only sends a copy of the thermal history data to control unit 20. Thus, the thermal history data of thermal control unit 20' still resides on thermal control unit 20' until a caregiver actively deletes its. When receiving the thermal history data from thermal control unit 20', controller 66 of thermal control unit 20 generates a message for display on display 40 of user interface 38 indicating whether the transmission of the thermal history data was successful or unsuccessful. If successful, controller 66 allows the caregiver to thereafter display all or a portion of the received thermal history data on display 40.

In some embodiments, one or both of controllers 66 or 66' of control units 20 and 20', respectively, are programmed to automatically prompt the caregiver to transfer prior thermal history data prior to commencing, or at the time of commencing, thermal treatment with the thermal control unit. The prompt reminds the caregiver to transfer any previous thermal treatment data, if it is exists, to the thermal control unit 20 currently being, or about to be, used with the patient. In some embodiments, the controller 66 or 66' prevents the thermal control unit 20 from being used to treat the patient until the caregiver either affirmatively indicates that no such prior thermal history data exists (e.g. this is the first thermal control unit being used with that patient) or the caregiver completes the transfer of thermal history data. In other embodiments, the prompt serves merely as a reminder for the caregiver who is free to respond to it or ignore it.

Figure 8:
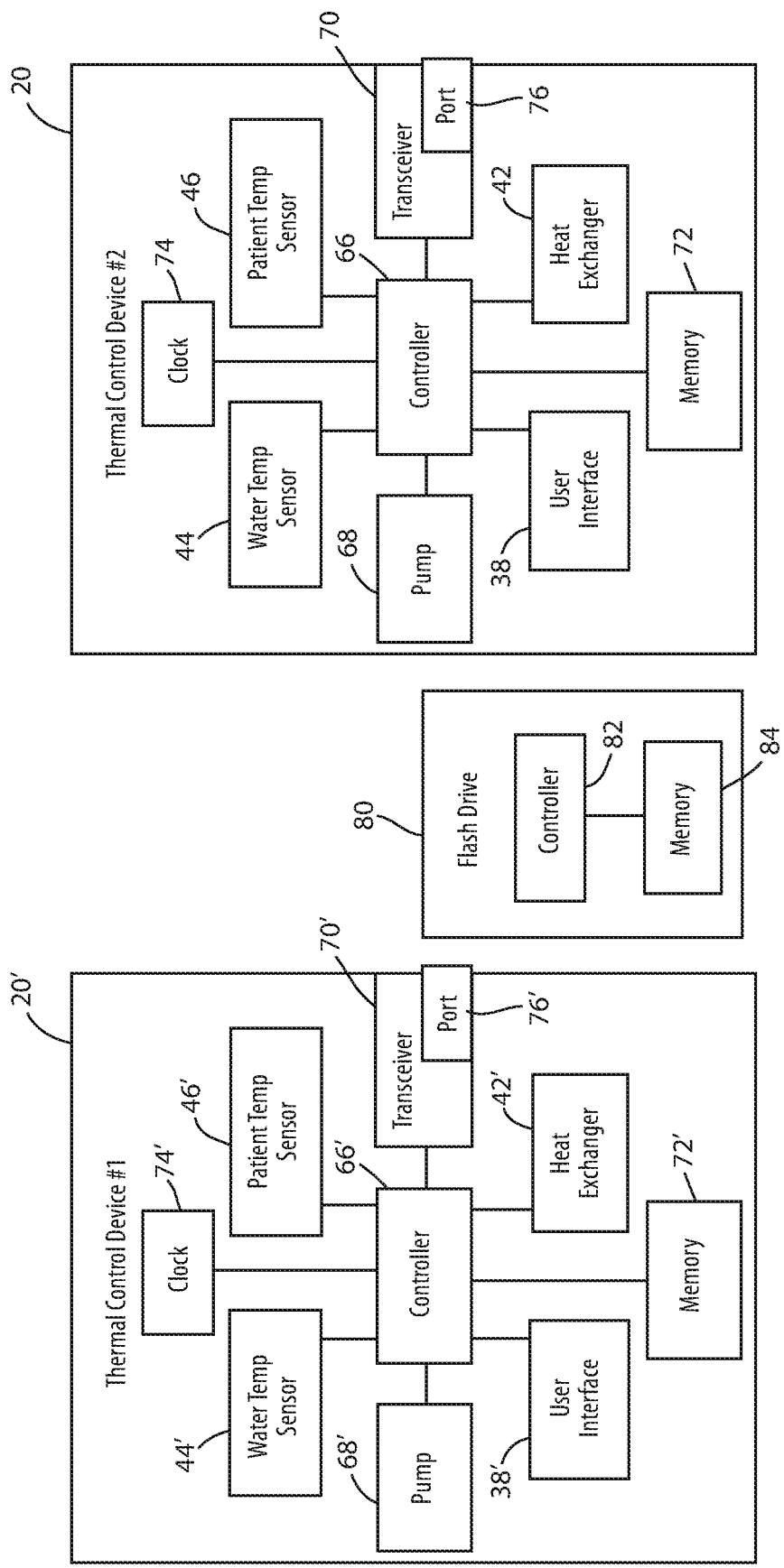
FIG. 8 is a block diagram of the electrical components of a pair of thermal control units and a flash drive illustrating a second manner for transferring thermal data between the thermal control units.

FIG. 8 illustrates an alternative manner in which thermal history data from a first thermal control unit 20' may be transferred to a second thermal control unit 20. In this example, thermal control units 20 and 20' include the same components as those discussed above with respect to the example of FIG. 7. However, instead of using a data cable 78 for transferring the thermal history data, a portable flash drive 80 is used. Portable flash drive 80 includes a controller 82 and a memory 84. In some embodiments, portable flash drive 80 is a conventional flash drive, such as a USB flash drive adapted to plug into a USB flash drive of a conventional computer. In other embodiments, flash drive 80 may be customized in terms of either its hardware or software (or both) so that it only operates in conjunction with thermal control units, such as units 20 and 20', and cannot be read by a conventional computer without the proper software (or hardware, or both).

In order to transfer the thermal history data between the thermal control units 20 and 20' of the example of FIG. 8, the caregiver first transfers the thermal history data of thermal control unit 20' to flash drive 80. Flash drive 80 receives this thermal history data and controller 82 stores this data in memory 84. Thereafter, the caregiver physically removes flash drive 80 from port 76' of thermal control unit 20' and physically inserts flash drive 80 into port 76 of thermal control unit 20. Once inserted into port 76, controller 66 reads the thermal history data from memory 84 and transfers it to memory 72 of thermal control unit 20. Controller 66 thereafter makes it available for display on display 40 of user interface 38.

Ports 76 and 76' of the example of FIG. 8 may be the same as ports 76 and 76' of the example of FIG. 7, or they may be modified in one or more manners so as to be able to connect to flash drive 80. Further, in some embodiments, thermal control unit 20' may be programmed to automatically save its thermal data in both memory 72' and memory 84 while thermal control unit 20' is being used to provide thermal treatment to a patient. In this manner, the caregiver does not need to undertake the extra manual step of instructing controller 66' to transfer the thermal history data to flash drive 80. Instead, whenever the caregiver is ready to transfer the thermal history data, he or she simply pulls flash drive 80 out of port 76' and inserts it into port 76. Because of the automatic saving by controller 66' of the thermal history data onto memory 84, flash drive 80 is ready to be removed without the caregiver having to wait for the transmission of the thermal history data to it.

In some embodiments, thermal control units 20 and/or 20' may be programmed to display a reminder on display 40 whenever therapy is commenced with these units and no flash drive 80 is detected by controller 66 (or 66') as being coupled to the corresponding port 76 (or 76'). In this manner, the caregiver is reminded to insert a flash drive 80 into the corresponding port so that automatic storage of the thermal data can be accomplished while the thermal therapy is being applied.

Flash drive 80 is stored, in some embodiments, in a pocket (now shown) integrated into thermal pad 30. The pocket is specifically dimensioned to receive the flash drive 80. Alternatively, the flash drive may include a physical cord, string, cable, or the like, that tethers the flash drive 80 to thermal pad 30 or thermal control unit 20'. Such a tether, however, is constructed so as to enable the user to easily remove it so that flash drive 80 can be easily transferred to a subsequent thermal control device 20.

Figure 9:
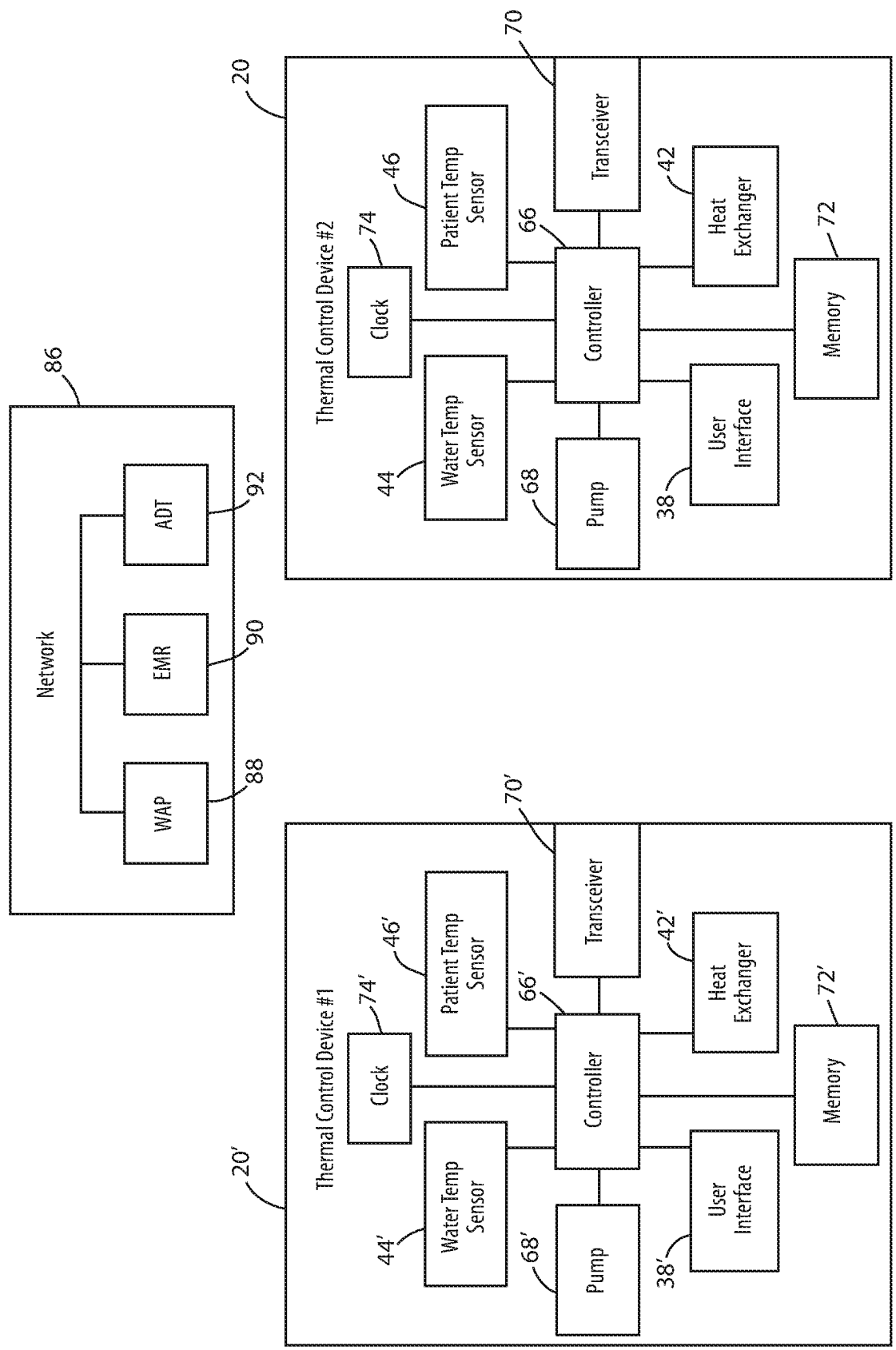
FIG. 9 is a block diagram of the electrical components of a pair of thermal control units and a local area network illustrating a third manner of transferring thermal data between the thermal control units.

FIG. 9 illustrates another alternative manner in which thermal history data from a first thermal control unit 20' may be transferred to a second thermal control unit 20. In this example, thermal control units 20 and 20' include all of the same components as those discussed above with respect to the example of FIGS. 7 and 8 with the exception of transceivers 70 and 70'. Transceivers 70 and 70' of the example of FIG. 9 are wireless transceivers adapted to transmit the thermal history data wirelessly so that a cable, such as data cable 78, does not need to be used. In one embodiment, transceivers 70 and 70' are Bluetooth transceivers (IEEE 802.15.1) that communicate directly with each other. In another embodiment, transceivers 70 and 70' are ZigBee transceivers (IEEE 802.15.4) that communicate directly with each other.

In the embodiment shown in FIG. 9, transceivers 70 and 70' are WiFi transceivers (IEEE 802.11) that communicate with each other via a local area network 86. More specifically, control units 20 and 20' communicate with one or more wireless access points 88 of local area network 86. One or more servers or services, such as an Electronic Medical Records (EMR) server 90 and an Admission, Discharge, and Transfer (ADT) server 92, may be coupled to the local area network 86.

In one embodiment, thermal control unit 20' transfers its thermal data to thermal control unit 20 by forwarding its thermal history data to EMR server 90, which stores the data as part of the electronic medical record for the particular patient being treated by thermal control unit 20'. Once it is stored in EMR server 90, thermal control unit 20 retrieves it by communicating with EMR server 90 (via WAP 88) and requesting the stored thermal history data. The thermal history data is then transmitted wirelessly through WAP 88 to thermal control unit 20.

In an alternative embodiment, one or both of the transceivers 70 and/or 70' are replaced with, or supplemented with, wired ports 76 that are able to communicate with local area network 86 using a wired connection, such as, but not limited to, a conventional Ethernet cable. In this alternative embodiment, the thermal history data from thermal control unit 20' can be uploaded to EMR server 90 via either a wired connection or a wireless connection, and the thermal history data can be downloaded from EMR server 90 to thermal control unit 20 either via a wired connection or a wireless connection.

In still another alternative embodiment, thermal control unit 20' of FIG. 9 communicates its thermal history data to thermal control unit 20 without storing the thermal history data in any servers on local area network 86. In this embodiment, local area network 86 acts merely as a conduit by which the thermal history data is passed from thermal control unit 20' to thermal control unit 20.

Figure 10:
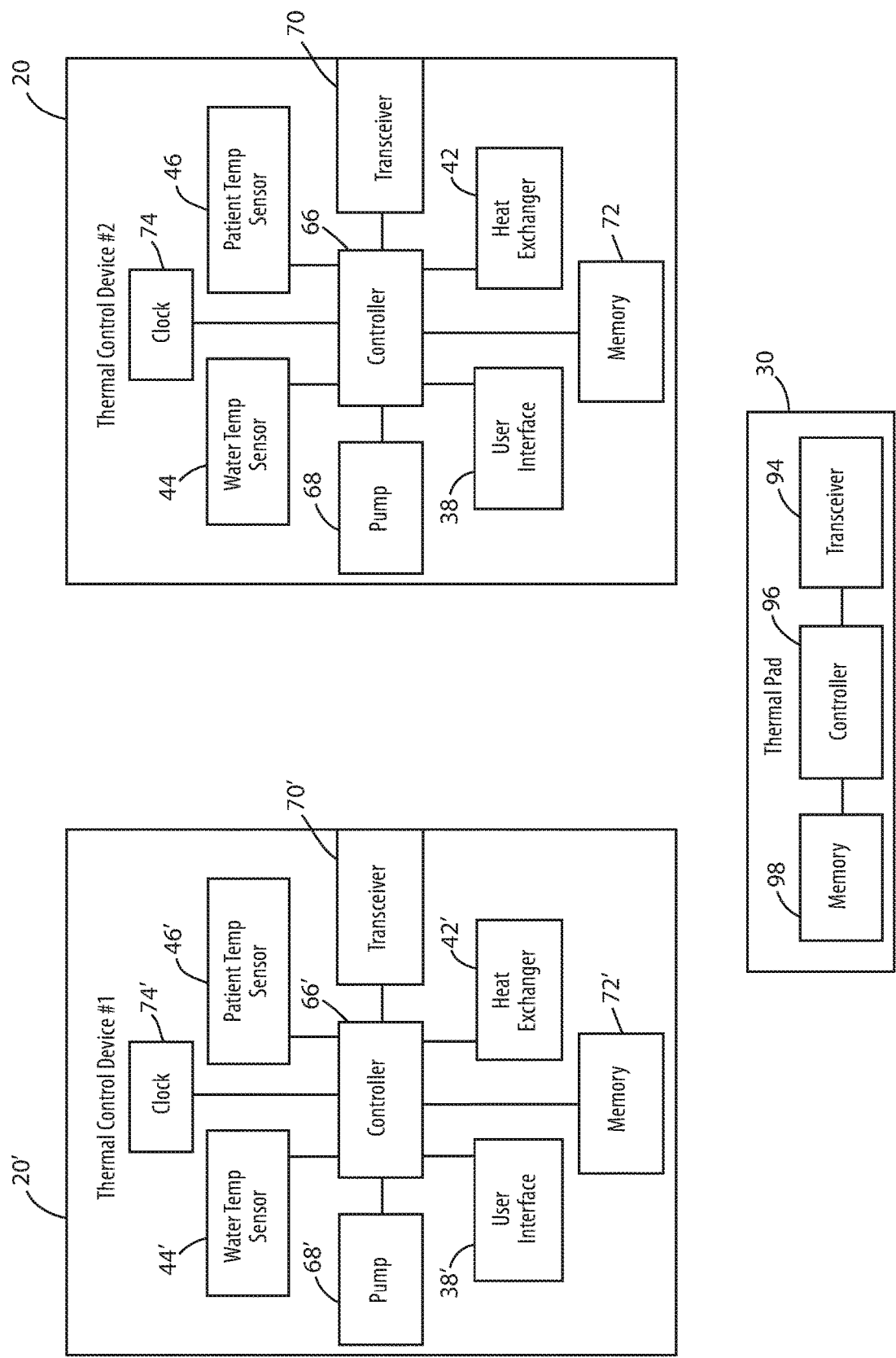
FIG. 10 is a block diagram of the electrical components of a pair of thermal control units and a thermal pad illustrating a fourth manner of transferring thermal data between the thermal control units.

FIG. 10 illustrates another alternative manner in which thermal history data from a first thermal control unit 20' may be transferred to a second thermal control unit 20. In this example, thermal control units 20 and 20' include all of the same components as those discussed above with respect to the example of FIGS. 7-9 with the sole possible exception of transceivers 70 and 70'. Transceivers 70 and 70' of the example of FIG. 10 are adapted to communicate with a transceiver 94 integrated into thermal pad 30. Depending upon the type of transceiver 94 integrated therein, transceivers 70 and/or 70' may be the same or different from the transceivers 70 and 70' previously described, as will be discussed more below.

During the thermal treatment of a patient utilizing thermal control unit 20' of FIG. 10, controller 66' transmits thermal data to thermal pad 30 utilizing a communication link between transceiver 70' and transceiver 94. When transceiver 94 receives the thermal data, controller 96 of thermal pad 30 stores the received thermal data in a memory 98 on board thermal pad 30. When the patient's thermal treatment is switched to thermal control unit 20, transceiver 94 of thermal pad 30 communicates the thermal history data stored in memory 98 to thermal control unit 20, which stores it in memory 72.

The communication link between transceivers 70' and 94, as well as the communication link between transceivers 94 and 70, may take on any of a variety of forms. In one embodiment, a cable, such as data cable 78, is coupled between transceivers 70 or 70' and transceiver 94. In another embodiment, transceivers 70 and/or 70' communicate wirelessly with transceiver 94, such as via Bluetooth, ZigBee, or utilizing a WiFi connection. In still another embodiment, transceivers 70, 70', and 94 are constructed so as to be able to communicate either wirelessly or via a wire, thereby giving the caregiver the option of whether to transfer the thermal history data by wire or wirelessly.

When transceiver 94 is adapted to be coupled to a cable for communicating with transceivers 70 and/or 70', the cable is integrated, in some embodiments, into hose 34 in order to avoid adding additional clutter between the thermal control units 20 or 20' and thermal pad 30. That is, the cable is attached to, or otherwise physically coupled to, one of the hoses 34 that run between thermal pad 30 and thermal control unit 20 or 20'. At least one end of the data cable, however, may be separated from the fluid lines 28a and 28b so that the caregiver can plug the ends of the data cable into a data port on thermal control unit 20 or 20' that is spaced from fluid outlet ports 22 and/or fluid inlet ports 24.

In still other alternative embodiments, the communication link between transceiver 70' and transceiver 94 may be different than the communication link between transceiver 70 and transceiver 94. For example, in one such alternative embodiment, thermal control unit 20' may communicate with thermal pad 30 via a wire while thermal pad 30 may communicate with thermal control unit 20 wirelessly, or vice versa. As another alternative, thermal pad 30 may have a USB port for communicating with a flash drive, such as flash drive 80 (not shown in FIG. 10). In such an embodiment, thermal control unit 20' communicates its thermal data to thermal pad 30 via a wired or wireless communication link between transceiver 70' and transceiver 94. In order to forward this thermal data from thermal pad 30 to thermal control unit 20, however, the user unplugs the flash drive from thermal pad 30 and plugs it into a USB port on thermal control unit 20. As yet another alternative, communication between thermal control unit 20' and thermal pad 30 may take place via a portable flash drive while communication between thermal control unit 20 and thermal pad 30 uses a wired or wireless connection.

Although thermal control units 20, 20', and thermal pads 30 have been described above as adapted to provide thermal therapy to a patient via a temperature controlled liquid, it will be understood by those skilled in the art that any one or more of these components could alternatively be configured to provide thermal treatment to the patient utilizing a temperature controlled gas.

Still further, it will be understood by those skilled in the art that one or more of thermal control units 20 or 20' may be integrated into another device. For example, in one embodiment, a patient support apparatus, such as a bed, includes a thermal control unit built into it that provides temperature controlled fluid for delivery to one or more thermal pads on the patient. One such example of a bed having a built in thermal control unit for controlling the temperature of a gas is disclosed in commonly assigned U.S. Pat. No. 8,011,039 issued to Stryker et al. and entitled PATIENT SUPPORT WITH UNIVERSAL ENERGY SUPPLY SYSTEM, the complete disclosure of which is incorporated herein by reference.

In any of the embodiments disclosed herein, thermal pad 30 may be a disposable pad. In some of those embodiments, the disposable thermal control pad 30 includes a port for receiving a flash drive 80 that is used to store the patient's thermal history data. Appropriate sensors and/or programming in the thermal pad 30 may issue an alert if the thermal pad 30 is removed from the patient prior to transferring the thermal history data to another device. The thermal pad 30 may also be modified so that it communicates both with a flash drive 80 and by one or more other means (e.g. a wireless connection or wired connection). In this manner, redundant pathways for transferring the thermal history data are provided.

In some of those embodiments of thermal control units 20 having a user interface, the user interface is configured to allow the user to select which thermal history data is recorded and/or transferred. In this manner, the user can customize the gathering of thermal data by the thermal control unit 20 and/or the transmitting of thermal history data from control unit 20 to another device.

Still further, in any of the embodiments disclosed herein, the thermal control units 20 and/or thermal pads 30 can be modified to communicate with one or more patient-worn devices, such as, but not limited, one or more patient sensors that sense information about the patient. Such sensors include sensors that sense movement of the patient and/or other aspects of the patient. Examples of such sensor units include the Fitbit sleep or activity tracker wristbands and/or bracelets manufactured by Fitbit, Inc. of San Francisco, Calif. Other types of sensors units can also communicate with the thermal control units 20 and/or thermal pad 30. Still further, thermal control units 20 and/or thermal pad 30 can be adapted in some embodiments to communicate with one or more devices that transmit identification information of the patient.

FIG. 11 illustrates another embodiment of a thermal control unit 120 according to another aspect of the present disclosure. Thermal control unit 120 is adapted to operate in any of the same manners described above with respect the thermal control unit 20 and/or 20' and to include any one or more of the features and functions described above with respect thermal control units 20 and 20'. Thermal control unit 120 differs from thermal control unit 20 in that thermal control unit 120 is adapted to communicate with a USB device 180. USB device 180 may be a flash drive, similar to flash drive 80, but may alternatively be a different type of USB device. When implemented as a flash drive, USB device 180 differs from flash drive 80 in that USB device 180 is programmed to automatically detect different modes in which it may be used. This different mode detection is carried out using conventional USB On-The-Go (OTG) technology, although other technology may be used in different embodiments. Such USB OTG technology allows device 180 to act as a slave device or a host device and to detect which one of these two roles it is to assume when it is connected to another USB OTG device. Thermal control unit 120 includes a USB OTG port (not shown) into which USB device 180 can be plugged and unplugged. This port is electrically coupled to USB OTG software that enables thermal control unit 120 and USB device 180 to communicate using USB OTG.

Thermal control unit 120 and USB device 180 communicate with each other in different modes when USB device 180 is physically coupled to the corresponding port on thermal control unit 120. In a first mode, thermal control unit 120 acts as a USB host device and writes thermal treatment data to device 180, which acts as a slave device. This thermal treatment data passed from thermal control unit 120 to USB device 180 includes, but is not limited to, any or all of the thermal data discussed previously (e.g. current and/or past patient target temperatures; current and/or past fluid target temperatures; patient and/or fluid temperature readings; treatment start and stop times; fluid flow rates; rates of change of patient and/or fluid temperatures; alarms or errors; device IDs; the patient's heart rate, breathing rate, oxygenation levels, other vital signs of the patient; medications administered; time of Return Of Spontaneous Circulation (ROSC); and/or a history and times of any one or more of these items, etc.). In a second mode, USB device 180 may act as a host device and treat a connected device as a slave.

In some embodiments, the thermal treatment data transferred from thermal control unit 120 to USB device 180 is transferred in a Comma Separated Value (CSV) format. In other embodiments, other formats are used for writing the data to USB device 180. Regardless of the format of the transferred data, thermal control unit 120 is configured to automatically detect when USB device 180 is coupled thereto and to transfer data to device 180 as the data is being generated during a patient's thermal treatment with thermal control unit 120 and/or as a batch of data previously generated during the patient's treatment with thermal control unit 120.

USB device 180, in some embodiments, is configured to couple to thermal control device 120 through a USB Serial Protocol Profile (SPP). In the embodiment shown in FIGS. 11 and 12, USB device 180 includes two ends: a first end 202 and a second end 204. First end 202 is a conventional USB plug that corresponds to the Type A standard connector of a conventional USB OTG connection, and second end 204 is a convention USB plug that corresponds to the Type B micro connector of a conventional USB OTG connection. In some embodiments, USB device 180 and thermal control unit 120 are configured to utilize the Host Negotiation Protocol that enables them to switch their host and slave roles. Still other protocols and/or features may be included with USB device 180 and/or thermal control unit 120.

In at least one embodiment, thermal control unit 120 is configured to automatically start transferring thermal treatment data to USB device 180 whenever it exits from a sleep mode and to terminate transferring thermal treatment data to USB device 180 whenever it enters the sleep mode. In such embodiments, if USB device 180 is not coupled to thermal control unit 120 upon exiting from sleep mode, thermal control unit 120 automatically starts saving the thermal data to a file on board thermal control unit 120. When USB device 180 is plugged into thermal control unit 120, thermal control unit 120 transfers the saved data file to device 180, as well as any treatment data that is contemporaneously occurring. If device 180 is not plugged into thermal control unit 120 during the treatment of a patient, thermal control unit 120 saves the thermal treatment data as a data file until unit 120 enters the sleep mode, and/or until a new patient is treated with thermal control unit 120. Once a USB device 180 is plugged into thermal control unit 120, the control unit 120 transfers all of its previously saved thermal data to device 180, including thermal data that may have been stored for multiple patients and/or for multiple sessions between sleep modes. In other embodiments, the data that is transferred to USB device 180 is configurable by a user via user interface 38.

USB device 180 also includes, in some embodiments, one or more configuration files that are read by thermal control unit 120 when it is plugged into control unit 120. The one or more configuration files include data indicating to thermal control unit 120 what thermal treatment data control unit 120 is to store during the thermal treatment of a patient using thermal control unit 120. Specifically, the one or more configuration files dictate to thermal control unit 120 what the variables are that the user wants to be captured during the operation of thermal control unit 120. Because different configuration files may be loaded on different devices and/or because USB device 180 can have different configuration files uploaded to it (discussed more below), thermal control unit 120 may store different thermal treatment data for different patients, or different thermal treatment data at different times, depending upon what configuration files were stored on USB device 180 and read by thermal control unit 120.

In order to read data transferred from thermal control unit 120 and stored on USB device 180, USB device 180 may be unplugged from thermal control unit 120 and plugged into a conventional computer, such as laptop 200 of FIG. 12. When plugged into computer 200, USB device 180 is seen by computer 200 as a flash drive. The user of laptop 200 is able to use conventional software programs to access and view the contents of USB device 180, such as, but not limited to, Windows Explorer (or another web browser) and see all of the CSV files (or other formatted files) that were saved during patient treatments. The user of computer 200 is able to copy the files from USB device 180 onto the computer 200 and manipulate, view, process, and/or print out the data from USB device 180, as desired.

When USB device 180 is plugged into a computer, such a computer 200, it may also or alternatively be used to store files transferred from computer 200. For example, a user of computer 200 may copy or write one or more configuration files to USB device 180 using conventional software on computer 200. These configuration files, as discussed above, are read by thermal control unit 120 when USB device 180 is plugged into thermal control unit 120. One use of such files is to instruct thermal control unit 120 what variables and/or data to record on USB device 180 during thermal treatment of patients. Each configuration file includes a specific name and a series of parameters that are specific to that configuration file.

Although thermal control unit 120 has been described herein specifically for use with USB device 180, it will be understood that thermal control unit 120 can be modified to operate in conjunction with other types of data devices that operate in a similar manner as USB device 180. For example, instead of communicating with a data device through a USB port, such as described above, thermal control unit 120 may additionally or alternatively be equipped with a Controller Area Network (CAN) port that communicates using a CAN bus when the data device is coupled to the port. The data communicated is the same as the previously described.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A thermal control unit for supplying temperature controlled fluid to a thermal pad, the thermal control unit comprising:
    a fluid outlet adapted to fluidly couple to a fluid supply line;
    a fluid inlet adapted to fluidly couple to a fluid return line;
    a heat exchanger;
    a pump for circulating the fluid from the fluid inlet through the heat exchanger and to the fluid outlet;
    a transceiver;
    a memory;
    a display; and
    a controller adapted to receive previous thermal history data from a secondary thermal device via the transceiver and to display the previous thermal history data on the display in a first manner, the previous thermal history data having been generated by the secondary thermal device during thermal treatment of a patient, wherein the controller is further adapted to record primary thermal history data generated by the thermal control unit during thermal treatment of the patient with the thermal control unit and to display the primary thermal history data on the display in a second manner, the first manner being different from the second manner such that a viewer of the display is provided a visual indication of whether displayed thermal history data corresponds to the primary thermal history data or the previous thermal history data; and wherein the controller is still further adapted to record a time at which the previous thermal history data was received from the secondary thermal device and to display the time on the display.

2. The thermal control unit of claim 1 wherein the previous thermal history data includes at least two of the following data items: a patient target temperature; a fluid target temperature; a plurality of previous patient temperature readings; a plurality of previous fluid temperature readings; a time at which previous thermal treatment started; a time at which previous thermal treatment ended; a flow rate of the fluid; a rate of change of a patient's temperature; a rate of change of the fluid's temperature; a time at which a plurality of temperature readings were taken; an alarm; and an identification of the secondary thermal device.

3. The thermal control unit of claim 1 further comprising a port in communication with the transceiver, the port adapted to receive a physical communication medium that delivers the previous thermal history data to the transceiver.

4. The thermal control unit of claim 1 wherein the controller is adapted to forward both the primary thermal history data and the previous thermal history data to another device.

5. The thermal control unit of claim 1 wherein the controller receives the previous thermal history data without any information identifying the patient to which the previous thermal history data corresponds.

6. The thermal control unit of claim 1 wherein the secondary thermal device is adapted to control a temperature of the patient being treated by the secondary thermal device.

7. The thermal control unit of claim 6 wherein the secondary thermal device includes a pump, a heat exchanger, and a fluid whose temperature is controlled by the heat exchanger of the secondary thermal device.

8. The thermal control unit of claim 6 wherein the controller is adapted to receive the previous thermal history data directly from the secondary thermal device.

9. The thermal control unit of claim 1 further comprising a user interface adapted to enable a user of the thermal control unit to allow or disallow receiving the previous thermal history data.

10. A thermal control unit for supplying temperature controlled fluid to a thermal pad, the thermal control unit comprising:
    a fluid outlet adapted to fluidly couple to a fluid supply line;
    a fluid inlet adapted to fluidly couple to a fluid return line;
    a heat exchanger;
    a pump for circulating the fluid from the fluid inlet through the heat exchanger and to the fluid outlet;
    a transceiver;
    a memory;
    a display; and
    a controller adapted to receive previous thermal history data from a secondary thermal device via the transceiver and to display the previous thermal history data on the display in a first manner, the previous thermal history data having been generated by the secondary thermal device during thermal treatment of a patient, wherein the controller is further adapted to record primary thermal history data generated by the thermal control unit during thermal treatment of the patient with the thermal control unit and to display the primary thermal history data on the display in a second manner, the first manner being different from the second manner such that a viewer of the display is provided a visual indication of whether displayed thermal history data corresponds to the primary thermal history data or the previous thermal history data;
    and wherein the controller is still further adapted to prevent the fluid from being pumped out of the fluid outlet until the previous thermal history data is received by the controller or a user provides an indication to the controller that no previous thermal history data is available.

11. The thermal control unit of claim 10 wherein the previous thermal history data includes at least two of the following data items: a patient target temperature; a fluid target temperature; a plurality of previous patient temperature readings; a plurality of previous fluid temperature readings; a time at which previous thermal treatment started; a time at which previous thermal treatment ended; a flow rate of the fluid; a rate of change of a patient's temperature; a rate of change of the fluid's temperature; a time at which a plurality of temperature readings were taken; an alarm; and an identification of the secondary thermal device.

12. The thermal control unit of claim 11 further comprising a port in communication with the transceiver, the port adapted to receive a physical communication medium that delivers the previous thermal history data to the transceiver.

13. The thermal control unit of claim 10 wherein the controller is adapted to forward both the primary thermal history data and the previous thermal history data to another device.

14. A thermal control unit for supplying temperature controlled fluid to a thermal pad, the thermal control unit comprising:
- a fluid outlet adapted to fluidly couple to a fluid supply line for the thermal pad;
- a fluid inlet adapted to fluidly couple to a fluid return line for the thermal pad;
- a heat exchanger;
- a pump for circulating the fluid from the fluid inlet through the heat exchanger and to the fluid outlet;
- a transceiver;
- a first memory;
- a controller adapted to record thermal data in the first memory relating to therapy applied to a patient using the thermal pad, the controller also adapted to transfer the thermal data via the transceiver to a second memory off-board the thermal control unit, the second memory being physically coupled to the thermal pad; and
- a clock in communication with the controller, wherein the controller is adapted to record a time at which the thermal data is transferred to the second memory and to forward the recorded time to the second memory.

15. The thermal control unit of claim 14 wherein the thermal data includes at least two of the following data items: a patient target temperature; a fluid target temperature; a patient temperature reading; a fluid temperature reading; a time at which thermal treatment started; a time at which thermal treatment ended; a flow rate of the fluid; a rate of change of the patient's temperature; a rate of change of the fluid's temperature; a time at which a temperature reading was taken; an alarm; and an identification of the thermal control unit.

16. The thermal control unit of claim 14 wherein the controller is further adapted to transfer an identifier identifying the thermal control unit to the second memory.

17. The thermal control unit of claim 16 wherein the controller is further adapted to prevent the fluid from being pumped out of the fluid outlet until the controller detects that the transceiver is in communication with the thermal pad.

* * * * *